United States Patent
Oda

(10) Patent No.: US 10,736,589 B2
(45) Date of Patent: Aug. 11, 2020

(54) RADIOGRAPHY APPARATUS, IMAGE PROCESSING APPARATUS, IMAGE PROCESSING METHOD, AND IMAGE PROCESSING PROGRAM

(71) Applicant: FUJIFILM CORPORATION, Minato-ku, Tokyo (JP)

(72) Inventor: Yasufumi Oda, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 345 days.

(21) Appl. No.: 15/974,722

(22) Filed: May 9, 2018

(65) Prior Publication Data

US 2018/0333113 A1 Nov. 22, 2018

(30) Foreign Application Priority Data

May 18, 2017 (JP) .................. 2017-099107

(51) Int. Cl.
| | | |
|---|---|---|
| *A61B 6/00* | (2006.01) | |
| *H04N 5/32* | (2006.01) | |
| *G01T 1/20* | (2006.01) | |
| *G01T 1/208* | (2006.01) | |

(Continued)

(52) U.S. Cl.
CPC .......... *A61B 6/4233* (2013.01); *A61B 6/4216* (2013.01); *A61B 6/482* (2013.01); *A61B 6/505* (2013.01); *A61B 6/5205* (2013.01); *A61B 6/5217* (2013.01); *A61B 6/5258* (2013.01); *G01T 1/208* (2013.01); *G01T 1/2012* (2013.01);

(Continued)

(58) Field of Classification Search
CPC ....... A61B 6/4233; A61B 6/482; A61B 6/505; A61B 6/4216; A61B 6/5205; A61B 6/5217; A61B 6/5258; A61B 6/00; A61B 6/582; H04N 5/3597; H04N 5/32; H04N 5/361; G01T 1/2012; G01T 1/208; G16H 50/30

See application file for complete search history.

(56) References Cited

U.S. PATENT DOCUMENTS

| 9,813,647 B2 * | 11/2017 | Kobayashi ................ G06T 5/40 |
| 10,595,804 B2 * | 3/2020 | Tajima ................ A61B 6/5217 |
| 2004/0258201 A1 * | 12/2004 | Hayashida ............ G01N 23/04 |
| | | 378/62 |

FOREIGN PATENT DOCUMENTS

| WO | 2011/093145 A1 | 8/2011 |
| WO | 2012/032801 A1 | 3/2012 |

* cited by examiner

*Primary Examiner* — David P Porta
*Assistant Examiner* — Meenakshi S Sahu
(74) *Attorney, Agent, or Firm* — Solaris Intellectual roperty Group, PLLC

(57) ABSTRACT

A control unit corrects a lag component, which is included in offset image data in a state in which radiation is not emitted for a period from the end of a first imaging operation of generating second radiographic image data in a state in which the radiation is emitted and to the start of a second imaging operation of generating the second radiographic image data in the state in which the radiation is emitted and at each of a plurality of different times elapsed since the first imaging operation, on the basis of a combination of the correction image data and the time elapsed since the first imaging operation, lag component time change information, and a time from the end of the first imaging operation to the start of the second imaging operation, and corrects the second radiographic image data using the corrected offset image data.

11 Claims, 11 Drawing Sheets

(51) Int. Cl.
*H04N 5/361* (2011.01)
*H04N 5/359* (2011.01)
(52) U.S. Cl.
CPC ............ *H04N 5/32* (2013.01); *H04N 5/3597* (2013.01); *H04N 5/361* (2013.01)

RADIOGRAPHY APPARATUS, IMAGE PROCESSING APPARATUS, IMAGE PROCESSING METHOD, AND IMAGE PROCESSING PROGRAM

CROSS-REFERENCE TO RELATED APPLICATION

This application claims priority under 35 USC 119 from Japanese Patent Application No. 2017-099107 filed May 18, 2017, the disclosure of which is incorporated by reference herein.

BACKGROUND

Technical Field

The present disclosure relates to a radiography apparatus, an image processing apparatus, an image processing method, and an image processing program.

Related Art

In the related art, a technique has been known which corrects, for example, a dark current component included in radiographic image data in a case in which the radiographic image data is generated using a radiation detector in which a plurality of pixels, each of which includes a conversion element that generates a larger amount of charge as it is irradiated with a larger amount of radiation, are arranged (see WO2011/093145A and WO2012/032801A).

SUMMARY

In addition, a technique has been known which derives information related to a subject on the basis of the detection results of each radiation detector in a radiography apparatus including two radiation detectors that are stacked in a radiation emission direction and are irradiated with radiations having different energy levels. In the radiography apparatus, for example, a first radiation detector that is provided on the irradiation side of the radiation (a side close to a radiation source) absorbs the radiation. Therefore, the amount of radiation that reaches a second radiation detector provided on a side of the first radiation detector from which the radiation is transmitted and emitted is reduced.

The technique according to the related art is not sufficient to improve the accuracy of correcting the radiographic image data generated by the second radiation detector.

The present disclosure is made in view of the above-mentioned problems and an object of the present disclosure is to provide a radiography apparatus, an image processing apparatus, an image processing method, and an image processing program that can improve the accuracy of correcting radiographic image data generated by a second radiation detector.

In order to achieve the object, the present disclosure provides a radiography apparatus comprising: a first radiation detector in which a plurality of pixels, each of which includes a conversion element that generates a larger amount of charge as it is irradiated with a larger amount of radiation, are arranged; a second radiation detector which is provided on a side of the first radiation detector, from which the radiation is transmitted and emitted, and in which a plurality of pixels, each of which includes a conversion element that generates a larger amount of charge as it is irradiated with a larger amount of radiation, are arranged; a first correction unit that corrects a first component, which varies depending on time in charge remaining in the plurality of pixels and is included in correction image data that is generated by the second radiation detector in a state in which the radiation is not emitted for a period from an end of a first imaging operation of generating radiographic image data using the second radiation detector in a state in which the radiation is emitted and to a start of a second imaging operation of generating radiographic image data using the second radiation detector in the state in which the radiation is emitted and at each of a plurality of different times elapsed since the first imaging operation, on the basis of a combination of the correction image data and the time elapsed since the first imaging operation, information indicating a change in the first component over time, and a time from the end of the first imaging operation to the start of the second imaging operation; and a second correction unit that corrects the radiographic image data generated from the second radiation detector by the second imaging operation using the correction image data corrected by the first correction unit.

In the radiography apparatus according to the present disclosure, the correction image data may include the first component and a second component that varies depending on temperature in the charge remaining in the plurality of pixels.

In the radiography apparatus according to the present disclosure, the correction image data may be generated at a time when a change in temperature after generation of previous correction image data is within an allowable range that is predetermined according to a variation in the second component with respect to the temperature.

In the radiography apparatus according to the present disclosure, in a case in which an amount of second component in the charge remaining in the pixels of the second radiation detector in the second imaging operation is equal to or less than a predetermined threshold value, the second correction unit may correct the radiographic image data generated from the second radiation detector by the second imaging operation, using the correction image data generated at a time closest to the second imaging operation, instead of the correction image data corrected by the first correction unit.

In the radiography apparatus according to the present disclosure, the correction image data may be generated at an interval at which a variation in the first component that is predetermined according to a change in the first component over time is equal to or greater than a threshold value.

In the radiography apparatus according to the present disclosure, the first correction unit may correct the first component included in the correction image data generated by the second radiation detector at a time closest to the second imaging operation.

The radiography apparatus according to the present disclosure may further comprise a third correction unit that corrects radiographic image data generated by the first radiation detector in the state in which the radiation is emitted, on the basis of correction image data generated by the first radiation detector in the state in which the radiation is not emitted.

The radiography apparatus according to the present disclosure may further comprise a derivation unit that derives information of a subject that is an imaging target, using the radiographic image data which has been generated by the second radiation detector and corrected by the second correction unit and the radiographic image data which has been generated by the first radiation detector and corrected by the third correction unit.

In the radiography apparatus according to the present disclosure, each of the first and second radiation detectors may comprise a substrate on which the plurality of pixels are formed and a light emitting layer that is irradiated with the radiation and emits light. In each light emitting layer of the first and second radiation detectors, at least one of a thickness of each light emitting layer, a diameter of particles with which each light emitting layer is filled and which are irradiated with the radiation and emit light, a multi-layered structure of the particles, a filling rate of the particles, a doping amount of activator, a material forming each light emitting layer, or a layer structure of each light emitting layer may be changed or a reflecting layer that reflects the light to a surface of each light emitting layer which does not face the substrate may be formed on each light emitting layer.

In order to achieve the object, the present disclosure provides an image processing apparatus that corrects radiographic image data generated by a second radiation detector of a radiography apparatus comprising a first radiation detector in which a plurality of pixels, each of which includes a conversion element that generates a larger amount of charge as it is irradiated with a larger amount of radiation, are arranged and the second radiation detector which is provided on a side of the first radiation detector, from which the radiation is transmitted and emitted, and in which a plurality of pixels, each of which includes a conversion element that generates a larger amount of charge as it is irradiated with a larger amount of radiation, are arranged. The image processing apparatus comprises: a first correction unit that corrects a first component, which varies depending on time in charge remaining in the plurality of pixels and is included in correction image data that is generated by the second radiation detector in a state in which the radiation is not emitted for a period from an end of a first imaging operation of generating radiographic image data using the second radiation detector in a state in which the radiation is emitted and to a start of a second imaging operation of generating radiographic image data using the second radiation detector in the state in which the radiation is emitted and at each of a plurality of different times elapsed since the first imaging operation, on the basis of a combination of the correction image data and the time elapsed since the first imaging operation, information indicating a change in the first component over time, and a time from the end of the first imaging operation to the start of the second imaging operation; and a second correction unit that corrects the radiographic image data generated from the second radiation detector by the second imaging operation using the correction image data corrected by the first correction unit.

In order to achieve the object, the present disclosure provides an image processing method that corrects radiographic image data generated by a second radiation detector of a radiography apparatus comprising a first radiation detector in which a plurality of pixels, each of which includes a conversion element that generates a larger amount of charge as it is irradiated with a larger amount of radiation, are arranged and the second radiation detector which is provided on a side of the first radiation detector, from which the radiation is transmitted and emitted, and in which a plurality of pixels, each of which includes a conversion element that generates a larger amount of charge as it is irradiated with a larger amount of radiation, are arranged. The image processing method comprises: correcting a first component, which varies depending on time in charge remaining in the plurality of pixels and is included in correction image data that is generated by the second radiation detector in a state in which the radiation is not emitted for a period from an end of a first imaging operation of generating radiographic image data using the second radiation detector in a state in which the radiation is emitted and to a start of a second imaging operation of generating radiographic image data using the second radiation detector in the state in which the radiation is emitted and at each of a plurality of different times elapsed since the first imaging operation, on the basis of a combination of the correction image data and the time elapsed since the first imaging operation, information indicating a change in the first component over time, and a time from the end of the first imaging operation to the start of the second imaging operation; and correcting the radiographic image data generated from the second radiation detector by the second imaging operation using the corrected correction image data.

In order to achieve the object, the present disclosure provides a non-transitory recording medium recording an image processing program that causes a computer to perform: correcting radiographic image data generated by a second radiation detector of a radiography apparatus comprising a first radiation detector in which a plurality of pixels, each of which includes a conversion element that generates a larger amount of charge as it is irradiated with a larger amount of radiation, are arranged and the second radiation detector which is provided on a side of the first radiation detector, from which the radiation is transmitted and emitted, and in which a plurality of pixels, each of which includes a conversion element that generates a larger amount of charge as it is irradiated with a larger amount of radiation, are arranged: correcting a first component, which varies depending on time in charge remaining in the plurality of pixels and is included in correction image data that is generated by the second radiation detector in a state in which the radiation is not emitted for a period from an end of a first imaging operation of generating radiographic image data using the second radiation detector in a state in which the radiation is emitted and to a start of a second imaging operation of generating radiographic image data using the second radiation detector in the state in which the radiation is emitted and at each of a plurality of different times elapsed since the first imaging operation, on the basis of a combination of the correction image data and the time elapsed since the first imaging operation, information indicating a change in the first component over time, and a time from the end of the first imaging operation to the start of the second imaging operation; and correcting the radiographic image data generated from the second radiation detector by the second imaging operation using the corrected correction image data.

According to the present disclosure, it is possible to improve the accuracy of correcting the radiographic image data generated by the second radiation detector.

BRIEF DESCRIPTION OF THE DRAWINGS

Exemplary Embodiments of the present invention will be described in detail with reference to the following figures, wherein.

DETAILED DESCRIPTION

Hereinafter, embodiments of the present disclosure will be described in detail with reference to the drawings.

First Embodiment

Figure 1:
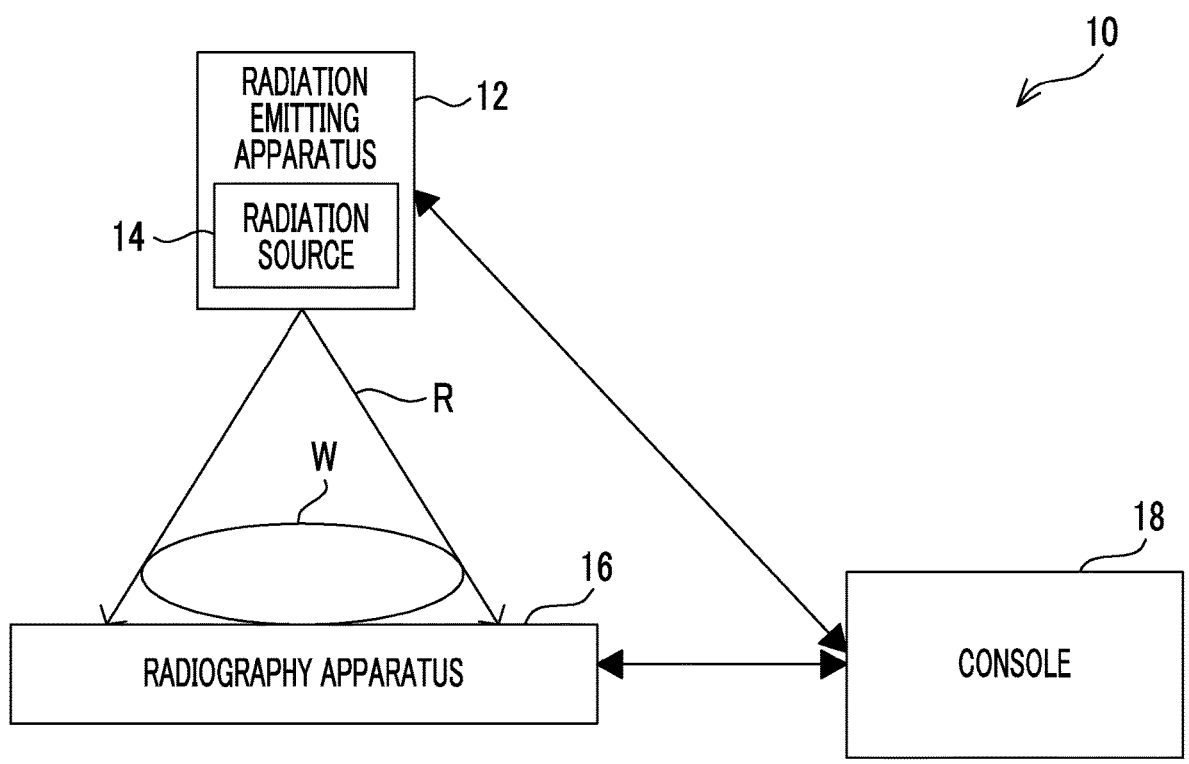
FIG. 1 is a block diagram illustrating an example of the configuration of a radiography system according to an embodiment.

First, the configuration of a radiography system 10 according to this embodiment will be described with reference to FIG. 1. As illustrated in FIG. 1, the radiography system 10 includes a radiation emitting apparatus 12, a radiography apparatus 16, and a console 18. In this embodiment, the console 18 is an example of an image processing apparatus according to the present disclosure.

The radiation emitting apparatus 12 according to this embodiment includes a radiation source 14 that irradiates a subject W, which is an example of an imaging target, with radiation R such as X-rays. An example of the radiation emitting apparatus 12 is a treatment cart. A method for commanding the radiation emitting apparatus 12 to emit the radiation R is not particularly limited. For example, in a case in which the radiation emitting apparatus 12 includes an irradiation button, a user, such as a radiology technician, may press the irradiation button to command the emission of the radiation R such that the radiation R is emitted from the radiation emitting apparatus 12. In addition, for example, the user, such as a radiology technician, may operate the console 18 to command the emission of the radiation R such that the radiation R is emitted from the radiation emitting apparatus 12.

When receiving the command to emit the radiation R, the radiation emitting apparatus 12 emits the radiation R from the radiation source 14 according to set exposure conditions, such as a tube voltage, a tube current, and an irradiation period. Hereinafter, the dose of the radiation R is simply referred to as "the amount of radiation".

Figure 2:
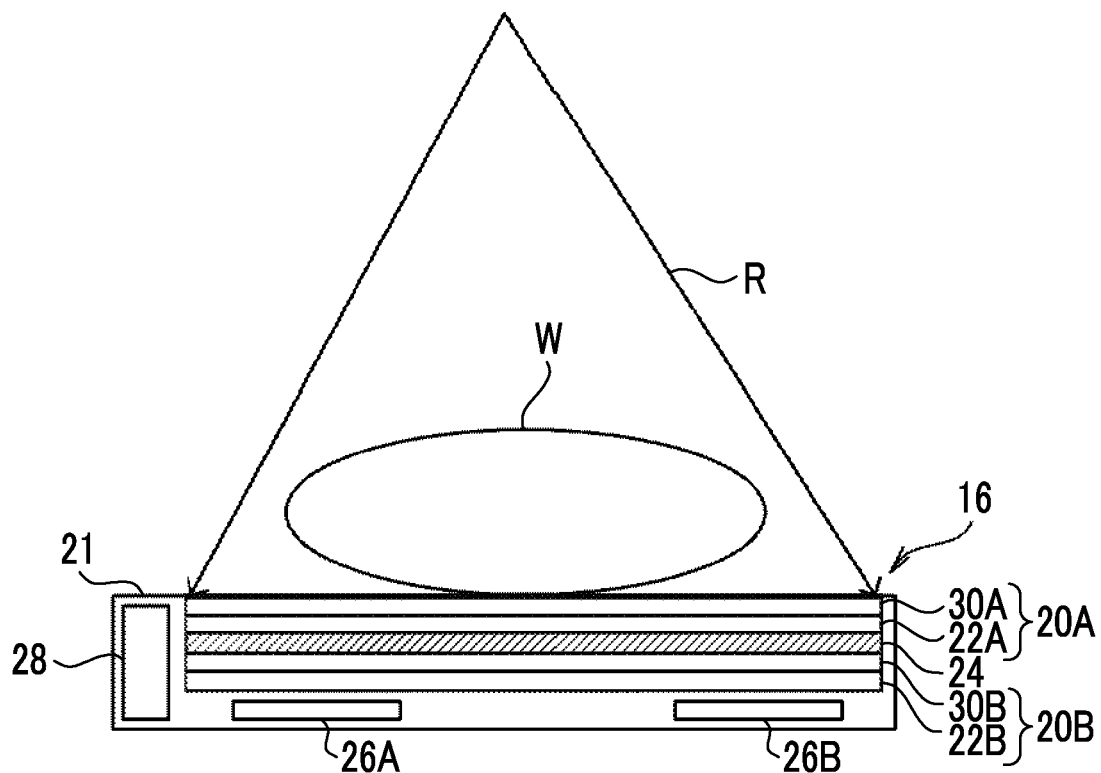
FIG. 2 is a side cross-sectional view illustrating an example of the configuration of a radiography apparatus according to the embodiment.

Next, the configuration of the radiography apparatus 16 according to this embodiment will be described with reference to FIG. 2. As illustrated in FIG. 2, the radiography apparatus 16 includes a plate-shaped housing 21 that transmits the radiation R and has a waterproof, antibacterial, and airtight structure. The housing 21 includes a first radiation detector 20A and a second radiation detector 20B that detect the radiation R transmitted through the subject W. In addition, the housing 21 includes a radiation limitation member 24, a control substrate 26A, a control substrate 26B, and a case 28. The radiography apparatus 16 captures radiographic images of the subject W using the first radiation detector 20A and the second radiation detector 20B. Hereinafter, in a case in which the first radiation detector 20A and the second radiation detector 20B do not need to be distinguished from each other, they are generically referred to as "radiation detectors 20".

The first radiation detector 20A is provided on the incident side of the radiation R in the radiography apparatus 16 and the second radiation detector 20B is provided so as to be stacked on the side of the first radiation detector 20A from which the radiation R is transmitted and emitted. The first radiation detector 20A includes a thin film transistor (TFT) substrate 30A and a scintillator 22A which is an example of a light emitting layer that is irradiated with the radiation R and emits light. The TFT substrate 30A and the scintillator 22A are stacked in the order of the TFT substrate 30A and the scintillator 22A from the incident side of the radiation R. The term "stacked" means a state in which the first radiation detector 20A and the second radiation detector 20B overlap each other in a case in which the first radiation detector 20A and the second radiation detector 20B are seen from the incident side or the emission side of the radiation R in the radiography apparatus 16 and it does not matter how they overlap each other. For example, the first radiation detector 20A and the second radiation detector 20B, or the first radiation detector 20A, the radiation limitation member 24, and the second radiation detector 20B may overlap while coming into contact with each other or may overlap with a gap therebetween in the stacking direction.

The second radiation detector 20B includes a TFT substrate 30B and a scintillator 22B which is an example of the light emitting layer. The TFT substrate 30B and the scintillator 22B are stacked in the order of the TFT substrate 30B and the scintillator 22B from the incident side of the radiation R.

That is, the first radiation detector 20A and the second radiation detector 20B are so-called irradiation side sampling (ISS) radiation detectors that are irradiated with the radiation R from the side of the TFT substrates 30A and 30B.

In the radiography apparatus 16 according to this embodiment, the scintillator 22A of the first radiation detector 20A and the scintillator 22B of the second radiation detector 20B have different compositions. Specifically, for example, the scintillator 22A includes CsI (Tl) (cesium iodide having thallium added thereto) as a main component and the scintillator 22B includes gadolinium oxysulfide (GOS) as a main component. GOS has a higher sensitivity to the high-energy radiation R than CsI. In addition, a combination of the composition of the scintillator 22A and the composition of the scintillator 22B is not limited to the above-mentioned example and may be, for example, a combination of other compositions or a combination of the same compositions.

For example, the scintillators 22A and 22B have emission characteristics that vary depending on a thickness. As the thickness increases, the amount of light emitted increases and sensitivity increases. However, image quality deteriorates due to, for example, light scattering.

For example, in a case in which the scintillators 22A and 22B are formed by being filled with particles which are irradiated with the radiation R and emit light, such as GOS particles, as the diameter of the particle increases, the amount of light emitted increases and sensitivity increases. However, the amount of light scattering increases and the increase in the amount of light scattering affects adjacent pixels 32, which results in the deterioration of image quality.

In addition, the scintillators 22A and 22B may have a stacked structure of a small-particle layer and a large-particle layer. For example, in a case in which each of the first radiation detector 20A and the second radiation detector 20B is irradiated with the radiation R from the scintillators 22A and 22B to the TFT substrates 30A and 30B unlike the radiography apparatus 16 according to this embodiment, image blurring is small in the scintillators 22A and 22B in which a region close to the irradiation side of the radiation R is filled with small particles and a region close to the side of the TFT substrate 30 that is the emission side of the radiation R is filled with large particles. However, oblique components of light that is radially emitted by the small particles are less likely to reach the TFT substrates 30A and 30B and sensitivity is reduced. In addition, in a case in which the ratio of the region filled with small particles to the region filled with large particles is changed such that the number of layers formed by the region filled with large particles is larger than the number of layers formed by the region filled with small particles, sensitivity increases. However, in this case, light scattering affects adjacent pixels 32, which results in the deterioration of image quality.

As the filling rate of the particles increases, the sensitivity of the scintillators 22A and 22B increases. However, the amount of light scattering increases and image quality deteriorates. Here, the filling rate is a value obtained by dividing the total volume of the particles of the scintillator 22A or 22B by the volume of the scintillator 22A or 22B and multiplying the divided value by 100 (the total volume of the particles of the scintillator 22A or 22B/the volume of the scintillator 22A or 22B×100). In addition, powder is treated in the scintillators 22A and 22B. Therefore, in a case in which the filling rate is greater than 80%, it is difficult to manufacture the scintillators 22A and 22B. For this reason, it is preferable that the filling rate is in the range of 50 vol % to 80 vol %.

In addition, the emission characteristics of the scintillators 22A and 22B vary depending on the doping amount of activator. As the doping amount of activator increases, the amount of light emitted tends to increase. However, the amount of light scattering increases and image quality deteriorates.

The emission characteristics of the scintillators 22A and 22B with respect to the radiation R vary depending on the material used for the scintillators 22A and 22B. For example, in a case in which each of the first radiation detector 20A and the second radiation detector 20B is irradiated with the radiation R from the scintillators 22A and 22B to the TFT substrates 30A and 30B unlike the radiography apparatus 16 according to this embodiment, the scintillator 22A is made of GOS and the scintillator 22B is made of CsI (Tl) in order to put emphasis on sensitivity in the scintillator 22A and to put emphasis on image quality in the scintillator 22B.

In addition, the emission characteristics of the scintillators 22A and 22B with respect to the radiation R vary depending on whether the scintillators 22A and 22B have a plate-shaped layer structure or a columnar separated layer structure.

For example, the scintillator 22A is configured to have the plate-shape layer structure and the scintillator 22B is configured to have the columnar separated layer structure in order to put emphasis on sensitivity in the scintillator 22A and to put emphasis on image quality in the scintillator 22B.

Figure 3:
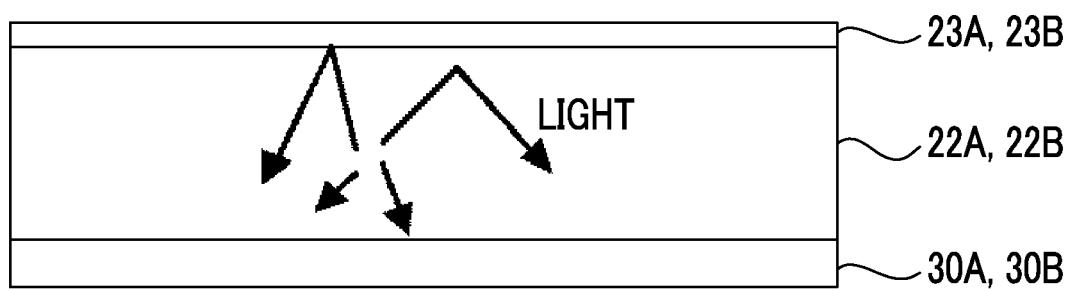
FIG. 3 is a cross-sectional view illustrating an example of a configuration in a case in which a reflecting layer is formed on a surface of a scintillator which is opposite to a TFT substrate.

In addition, as illustrated in FIG. 3, reflecting layers 23A and 23B that transmit the radiation R and reflect visible light are formed on the sides of the TFT substrates 30A and 30B which are opposite to the scintillators 22A and 22B to effectively guide light generated by the scintillators 22A and 22B to the TFT substrates 30A and 30B. Therefore, sensitivity is improved. A method for providing the reflecting layers 23A and 23B is not particularly limited. For example, any of a sputtering method, a vapor deposition method, and a coating method may be used to form the reflecting layers. It is preferable that the reflecting layers 23A and 23B are made of a material with high reflectance in an emission wavelength range of the scintillators 22A and 22B used. For example, the reflecting layers are made of Au, Ag, Cu, Al, Ni, and Ti. For example, in a case in which the scintillators 22A and 22B are made of GOS:Tb, the reflecting layers are preferably made of Ag, Al, and Cu that have high reflectance in a wavelength of 400 nm to 600 nm. In a case in which the thickness of the reflecting layers is less than 0.01 μm, reflectance is not obtained. Even in a case in which the thickness is greater than 3 μm, the effect of further improving the reflectance is not obtained. For this reason, it is preferable that the thickness of the reflecting layers is in the range of 0.01 μm to 3 μm.

Therefore, the characteristics of the scintillators 22A and 22B may vary depending on a change in the diameter of particles, the multi-layered structure of the particles, the filling rate of the particles, the doping amount of activator, a material, and a layer structure and the formation of the reflecting layers 23A and 23B.

The radiation limitation member 24 that limits the transmission of the radiation R is provided between the first radiation detector 20A and the second radiation detector 20B. An example of the radiation limitation member 24 is a plate-shaped member made of, for example, copper or tin. It is preferable that a variation in the thickness of the radiation limitation member 24 in the incident direction of the radiation R is equal to or less than 1% in order to uniformize the limitation (transmittance) of the radiation. In a case in which the first radiation detector 20A sufficiently absorbs the radiation R, the radiation limitation member 24 may not be provided.

The control substrate 26A is provided so as to correspond to the first radiation detector 20A and electronic circuits, such as an image memory 56A and a control unit 58A which will be described below, are formed on the control substrate 26A. The control substrate 26B is provided so as to correspond to the second radiation detector 20B and electronic circuits, such as an image memory 56B and a control unit 58B which will be described below, are formed on the control substrate 26B. The control substrate 26A and the control substrate 26B are provided on the side of the second radiation detector 20B which is opposite to the incident side of the radiation R.

The case 28 is provided at a position (that is, outside the range of an imaging region) that does not overlap the radiation detector 20 at one end of the housing 21. For example, a power supply unit 70 which will be described below is accommodated in the case 28. The installation position of the case 28 is not particularly limited. For example, the case 28 may be provided at a position that overlaps the radiation detector 20 on the side of the second radiation detector 20B which is opposite to the incident side of the radiation.

Figure 4:
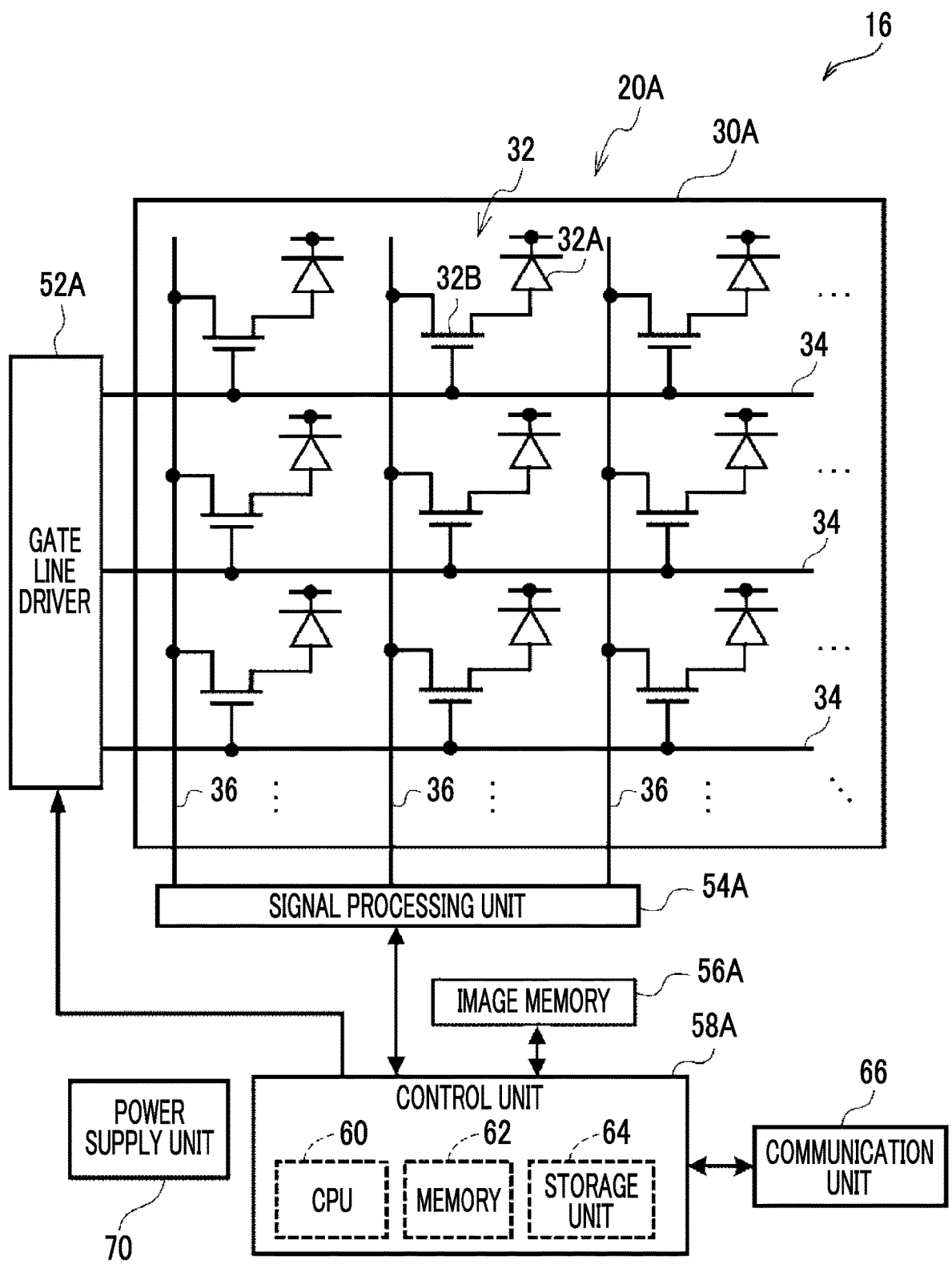
FIG. 4 is a block diagram illustrating an example of the configuration of a main portion of an electric system of a first radiation detector in the radiography apparatus according to the embodiment.
Figure 5:
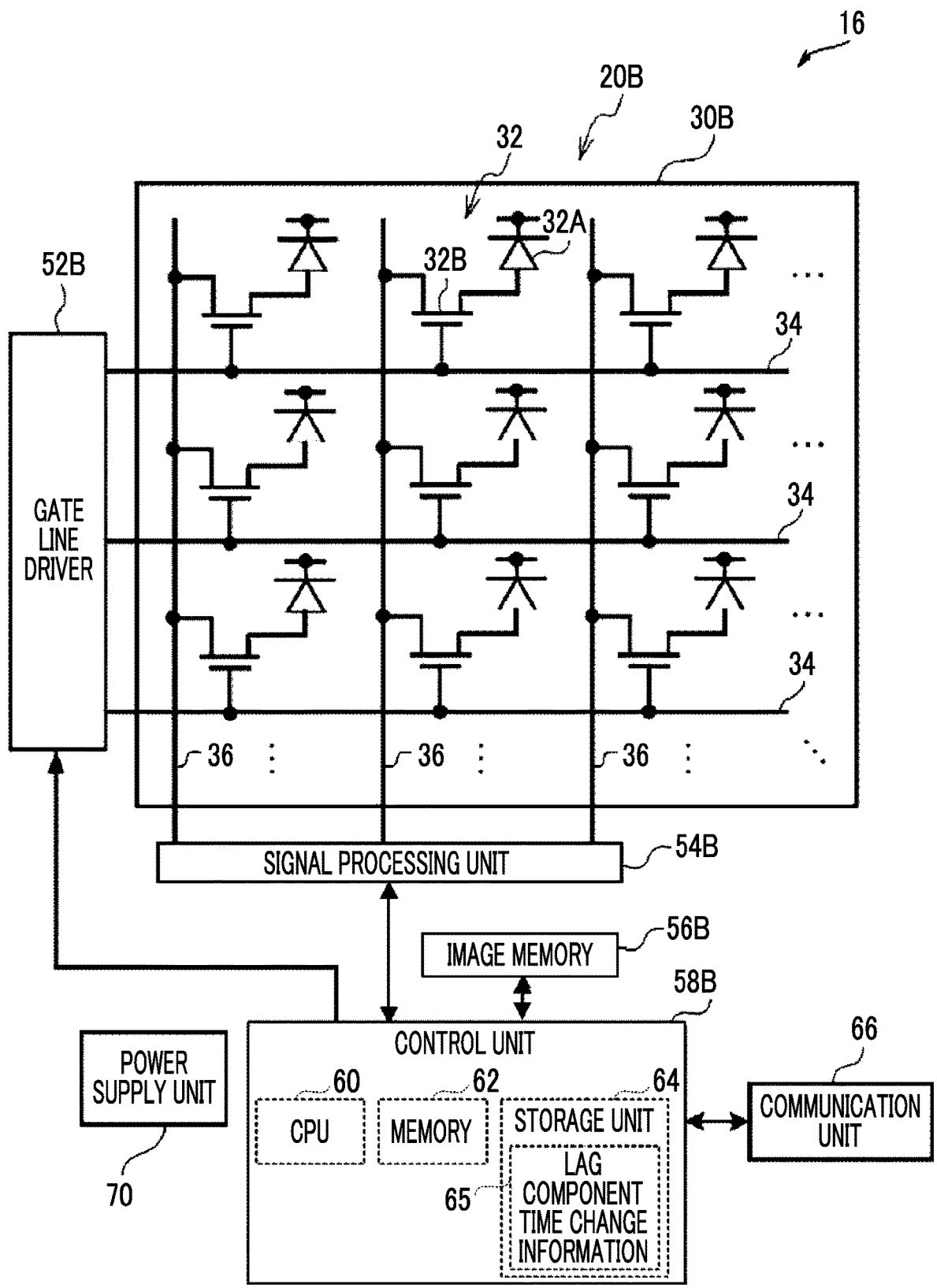
FIG. 5 is a block diagram illustrating an example of the configuration of a main portion of an electric system of a second radiation detector in the radiography apparatus according to the embodiment.

Next, the configuration of a main portion of an electric system of the radiography apparatus 16 according to this embodiment will be described with reference to FIGS. 4 and 5. FIG. 4 is a block diagram illustrating an example of the configuration of a main portion of the electric system of the radiography apparatus related to the first radiation detector 20A and FIG. 5 is a block diagram illustrating an example of the configuration of a main portion of the electric system of the radiography apparatus related to the second radiation detector 20B.

As illustrated in FIG. 4, a plurality of pixels 32 are two-dimensionally provided in one direction (a row direction in FIG. 4) and a cross direction (a column direction in FIG. 4) that intersects the one direction on the TFT substrate 30A. The pixel 32 includes a sensor unit 32A and a field effect thin film transistor (TFT; hereinafter, simply referred to as a "thin film transistor") 32B.

The sensor unit 32A includes, for example, an upper electrode, a lower electrode, and a photoelectric conversion film which are not illustrated, absorbs the light emitted from the scintillator 22A, generates charge, and accumulates the generated charge. The thin film transistor 32B reads the charge accumulated in the sensor unit 32A, converts the charge into an electric signal, and outputs the electric signal in response to a control signal. The sensor unit 32A is an example of a conversion element that generates a larger amount of charge as the amount of radiation becomes larger.

A plurality of gate lines 34 which extend in the one direction and are used to turn each thin film transistor 32B on and off are provided on the TFT substrate 30A. In addition, a plurality of data lines 36 which extend in the cross direction and are used to read out the charge through the thin film transistors 32B in an on state are provided on the TFT substrate 30A.

A gate line driver 52A is provided on one side of two adjacent sides of the TFT substrate 30A and a signal processing unit 54A is provided on the other side. Each gate line 34 of the TFT substrate 30A is connected to the gate line driver 52A and each data line 36 of the TFT substrate 30A is connected to the signal processing unit 54A.

The thin film transistors 32B corresponding to each gate line 34 on the TFT substrate 30A are sequentially turned on (in units of rows illustrated in FIG. 4 in this embodiment) by control signals which are supplied from the gate line driver 52A through the gate lines 34. Then, the charge which has been read by the thin film transistor 32B in an on state is transmitted as an electric signal through the data line 36 and is input to the signal processing unit 54A. In this way, charge is sequentially read from each gate line 34 (in units of rows illustrated in FIG. 4 in this embodiment) and image data indicating a two-dimensional radiographic image is acquired.

The signal processing unit 54A includes amplifying circuits (not illustrated) for amplifying an input electric signal and sample-and-hold circuits (not illustrated) which are provided for each data line 36. The electric signal transmitted through each data line 36 is amplified by the amplifying circuit and is then held by the sample-and-hold circuit. A multiplexer and an analog/digital (A/D) converter are connected to the output side of the sample-and-hold circuit in this order. The electric signals held by each sample-and-hold circuit are sequentially (serially) input to the multiplexer and are sequentially selected by the multiplexer. Then, the selected electric signal is converted into digital image data by the A/D converter.

The control unit 58A which will be described below is connected to the signal processing unit 54A. The image data output from the A/D converter of the signal processing unit 54A is sequentially output to the control unit 58A. The image memory 56A is connected to the control unit 58A. The image data sequentially output from the signal processing unit 54A is sequentially stored in the image memory 56A under the control of the control unit 58A. The image memory 56A has memory capacity that can store a predetermined amount of image data. Whenever a radiographic image is captured, captured image data is sequentially stored in the image memory 56A.

The control unit 58A includes a central processing unit (CPU) 60, a memory 62 including, for example, a read only memory (ROM) and a random access memory (RAM), and a non-volatile storage unit 64 such as a flash memory. An example of the control unit 58A is a microcomputer. In this embodiment, a first image processing program, which will be described below, is stored in the memory 62.

A communication unit 66 is connected to the control unit 58A and transmits and receives various kinds of information to and from external apparatuses, such as the radiation emitting apparatus 12 and the console 18, using at least one of wireless communication or wired communication. The power supply unit 70 supplies power to each of the above-mentioned various circuits or elements (for example, the gate line driver 52A, the signal processing unit 54A, the image memory 56A, the control unit 58A, and the communication unit 66). In FIG. 4, lines for connecting the power supply unit 70 to various circuits or elements are not illustrated in order to avoid complication.

As illustrated in FIG. 5, components of the TFT substrate 30B, the gate line driver 52B, the signal processing unit 54B, the image memory 56B, and the control unit 58B of the second radiation detector 20B have the same configurations as the corresponding components of the first radiation detector 20A except that lag component time change information 65 (which will be described in detail below) is stored in the storage unit 64 of the control unit 58B and a second image processing program, which will be described below, is stored in the memory 62. Therefore, the description thereof will not be repeated here. In addition, the control unit 58A and the control unit 58B are connected such that they can communicate with each other.

With the above-mentioned configuration, the radiography apparatus 16 according to this embodiment captures radiographic images using the first radiation detector 20A and the second radiation detector 20B. Hereinafter, the radiographic image captured by the first radiation detector 20A is referred to as a "first radiographic image" and image data indicating the first radiographic image is referred to as "first radiographic image data". In addition, hereinafter, the radiographic image captured by the second radiation detector 20B is referred to as a "second radiographic image" and image data indicating the second radiographic image is referred to as "second radiographic image data".

Figure 6:
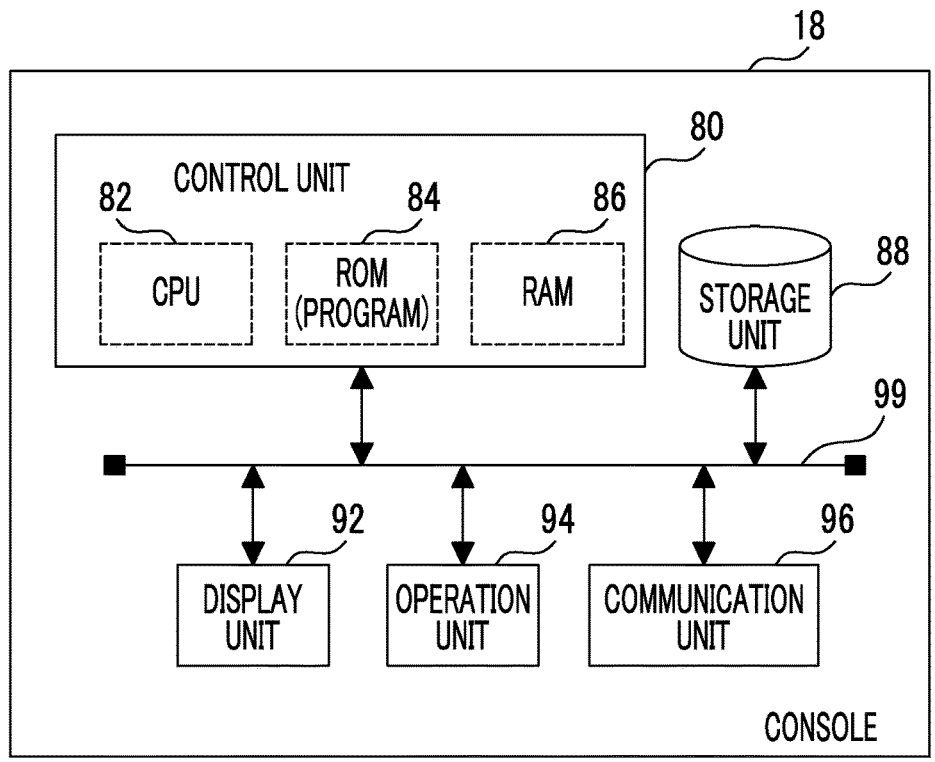
FIG. 6 is a block diagram illustrating an example of the configuration of a main portion of an electric system of a console according to the embodiment.

Next, the configuration of the console 18 according to this embodiment will be described with reference to FIG. 6. As illustrated in FIG. 6, the console 18 includes a control unit 80. The control unit 80 includes a CPU 82 that controls the overall operation of the console 18, a ROM 84 in which, for example, various programs or various parameters are stored in advance, and a RAM 86 that is used as, for example, a work area when the CPU 82 executes various programs.

In addition, the console 18 includes a non-volatile storage unit 88 such as a hard disk drive (HDD). The storage unit 88 stores and holds image data indicating the radiographic image captured by the first radiation detector 20A, image data indicating the radiographic image captured by the second radiation detector 20B, and various other data items.

The console 18 further includes a display unit 92, an operation unit 94, and a communication unit 96. The display unit 92 displays, for example, information related to imaging and a captured radiographic image. The operation unit 94 is used by a user to input a command to capture a radiographic image and a command to perform image processing for the captured radiographic image. For example, the operation unit 94 may have the form of a keyboard or the form of a touch panel integrated with the display unit 92. The communication unit 96 transmits and receives various kinds of information to and from the radiography apparatus 16 and the radiation emitting apparatus 12, using at least one of wireless communication or wired communication. In addition, the communication unit 96 transmits and receives various kinds of information to and from the external systems, such as a picture archiving and communication system (PACS) and a radiology information system (RIS), using at least one of wireless communication or wired communication.

The control unit 80, the storage unit 88, the display unit 92, the operation unit 94, and the communication unit 96 are connected to each other through a bus 99.

In the radiography apparatus 16 according to this embodiment, since the first radiation detector 20A and the radiation limitation member 24 absorb the radiation R, the amount of radiation that reaches the second radiation detector 20B is less than the amount of radiation that reaches the first radiation detector 20A. In addition, the radiation limitation member 24 generally has the characteristic that it absorbs a larger number of soft-ray components than hard-ray components in energy forming the radiation R, which depends on the material forming the radiation limitation member 24. Therefore, the energy distribution of the radiation R that reaches the second radiation detector 20B has a larger number of hard-ray components than the energy distribution of the radiation R that reaches the first radiation detector 20A.

In this embodiment, for example, about 50% of the radiation R that has reached the first radiation detector 20A is absorbed by the first radiation detector 20A and is used to capture a radiographic image. In addition, about 60% of the radiation R that has passed through the first radiation detector 20A and reached the radiation limitation member 24 is absorbed by the radiation limitation member 24. About 50% of the radiation R that has passed through the first radiation detector 20A and the radiation limitation member 24 and reached the second radiation detector 20B is absorbed by the second radiation detector 20B and is used to capture a radiographic image. Since the absorptivity of radiation by the radiation detector 20 and the radiation limitation member 24 varies depending on the energy of the radiation R, the shape of a spectrum changes.

That is, the amount of radiation used by the second radiation detector 20B to capture a radiographic image is about 20% of the amount of radiation used by the first radiation detector 20A to capture a radiographic image. In addition, the ratio of the amount of radiation used by the second radiation detector 20B to capture a radiographic image to the amount of radiation used by the first radiation detector 20A to capture a radiographic image is not limited to the above-mentioned ratio. However, it is preferable that the amount of radiation used by the second radiation detector 20B to capture a radiographic image is equal to or greater than 10% of the amount of radiation used by the first radiation detector 20A to capture a radiographic image in terms of diagnosis.

Figure 7:
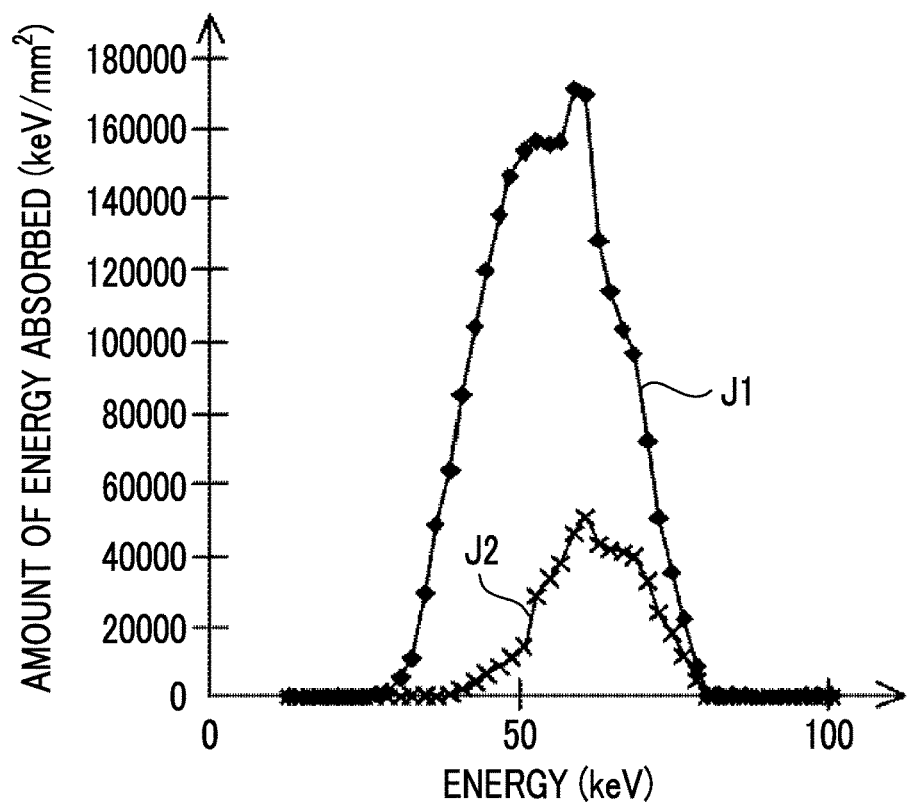
FIG. 7 is a graph illustrating the amount of radiation that reaches each of the first radiation detector and the second radiation detector.

Low-energy components of the radiation R are absorbed first. The radiation R absorbed by each of the first radiation detector 20A and the second radiation detector 20B will be described with reference to FIG. 7. In FIG. 7, the vertical axis indicates the amount of radiation R absorbed per unit area and the horizontal axis indicates the energy of the radiation R in a case in which the tube voltage of the radiation source 14 is 80 kV. In addition, in FIG. 7, a solid line J1 indicates the relationship between the energy of the radiation R absorbed by the first radiation detector 20A and the amount of radiation R absorbed per unit area. In addition, in FIG. 7, a solid line J2 indicates the relationship between the energy of the radiation R absorbed by the second radiation detector 20B and the amount of radiation R absorbed per unit area. Since the low-energy components of the radiation R are absorbed first, for example, as illustrated in FIG. 7, the energy components of the radiation R that reaches the second radiation detector 20B do not include the low-energy components of the energy components of the radiation R that reaches the first radiation detector 20A. That is, the energy of the radiation R emitted to the first radiation detector 20A is different from the energy of the radiation R emitted to the second radiation detector 20B through the first radiation detector 20A. Therefore, in the radiography apparatus 16 according to this embodiment, the radiation detectors 20 are irradiated with the radiations R having different energy levels and radiographic images are generated by the radiation detectors 20.

The console 18 according to this embodiment acquires radiographic image data generated by the radiation detectors 20 irradiated with the radiations R having different energy levels (radiation R with a first energy level and radiation R with a second energy level). In addition, the console 18 derives the ratio of the values of the corresponding pixels of first radiographic image data and second radiographic image data and generates image data for deriving the bone density of the subject W. Hereinafter, the image data for deriving the bone density of the subject W is referred to as "dual-energy X-ray absorptiometry (DXA) image data" and an image indicated by the DXA image data is referred to as a "DXA image". Specifically, the console 18 performs log conversion for each pixel value of each of the first radiographic image data and the second radiographic image data. Then, the console 18 subtracts image data obtained by performing log conversion for the second radiographic image data from image data obtained by performing log conversion for the first radiographic image data for each corresponding pixel to generate DXA image data. As such, the DXA image according to this embodiment is an example of a difference image for derivation according to the present disclosure.

Figure 8:
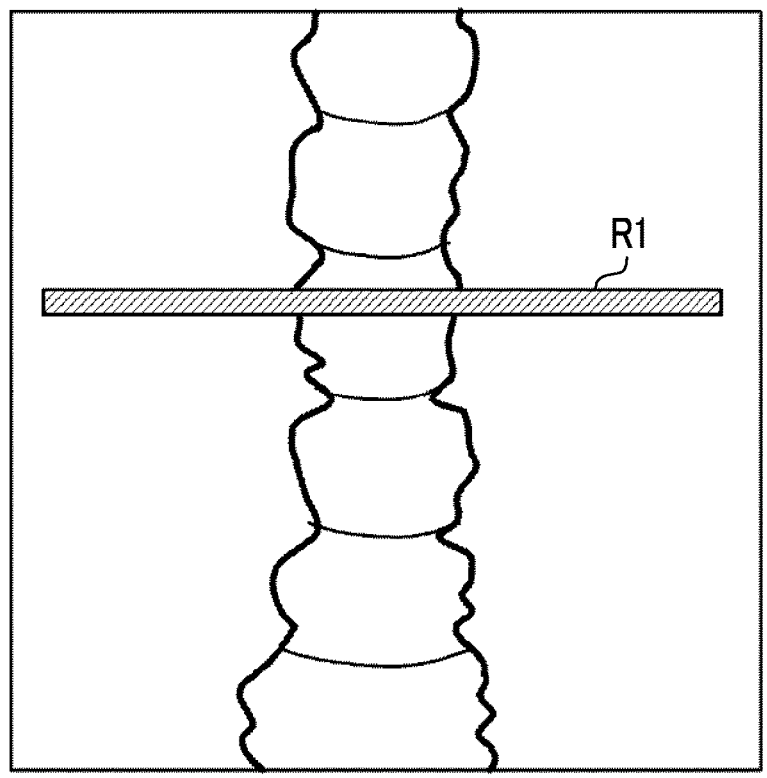
FIG. 8 is a front view illustrating an example of a region from which a DXA profile used to derive bone density is to be derived.

In addition, for example, as illustrated in FIG. 8, the console 18 according to this embodiment derives bone density from each pixel value (that is, the ratio of the values of the corresponding pixels of the first radiographic image and the second radiographic image) of the bone of the subject W in the cross-sectional direction (the horizontal direction in the example illustrated in FIG. 8) in the DXA image.

Figure 9:
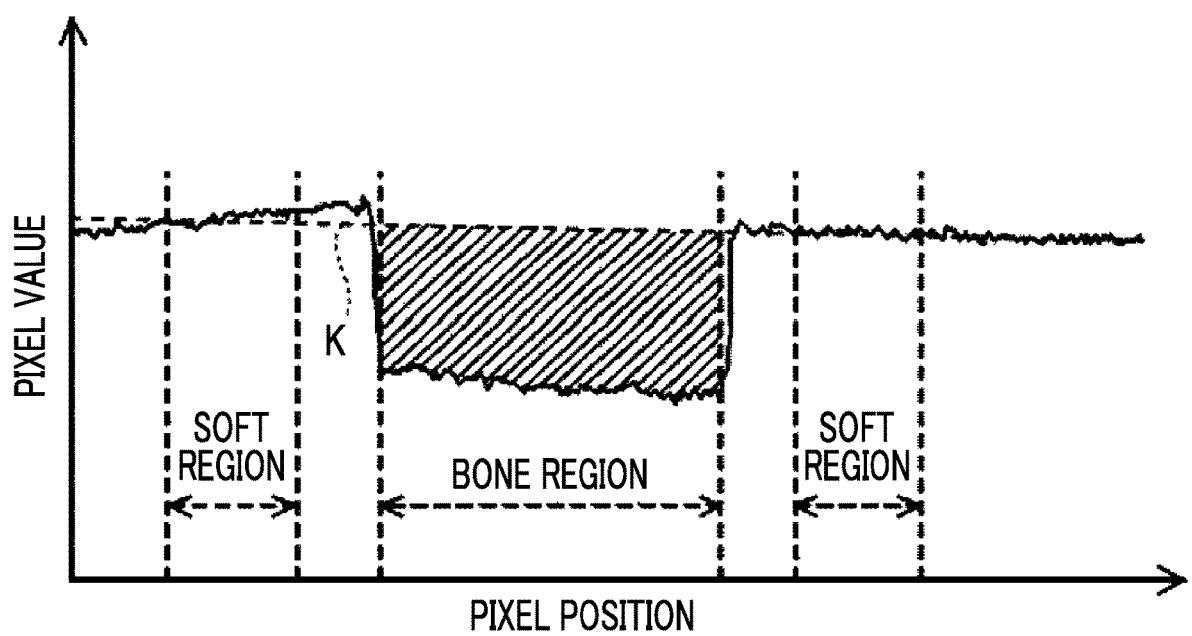
FIG. 9 is a graph illustrating a bone density derivation process.

FIG. 9 illustrates the value of each pixel in a derivation region R1 of the DXA image illustrated in FIG. 8. In FIG. 9, the horizontal axis indicates a pixel position in the horizontal direction of FIG. 8. In addition, in FIG. 9, the vertical axis indicates an average value of the values of a plurality of pixels in the vertical direction of FIG. 8 at each pixel position in the horizontal direction of FIG. 8. Hereinafter, a data group of the pixel values at each pixel position along the horizontal direction of FIG. 8 which is illustrated in FIG. 9 is referred to as a "DXA profile". In addition, a curve indicating the DXA profile is referred to as a profile curve (see a profile curve Pdxa in FIG. 10). That is, the DXA profile is a difference image between the first radiographic image and the second radiographic image and indicates a correspondence relationship between a pixel position and a pixel value in the derivation region R including a region corresponding to a soft tissue and a region corresponding to a bone tissue in the DXA image used to derive bone density.

As illustrated in FIG. 9, for the pixel values in the DXA profile, a pixel value at a pixel position corresponding to the bone tissue of the subject W is less than a pixel value at a pixel position corresponding to the soft tissue. The console 18 according to this embodiment derives the average value of the pixel values in soft tissue regions (hereinafter, referred to as "soft regions") on both sides of a bone tissue region (hereinafter, referred to as a "bone region") and derives a straight line (hereinafter, referred to as a "reference line") K that connects the average values derived at the pixel positions in a central portion of each soft region. In addition, the console 18 adds the differences between the reference line K and the pixel values at each pixel position in the bone region to derive the area of the bone region (the area of a hatched portion illustrated in FIG. 9). The area is a value corresponding to the bone mass of the subject W. For example, the bone region is separated from the soft region by a predetermined number of pixels in FIG. 9 in order to prevent the influence of noise caused by rays scattered by the bone.

In addition, the console 18 divides the derived area by the number of pixels corresponding to the width of the bone region to derive the difference between the pixel values of the bone region and the soft region per unit number of pixels. The difference is a value corresponding to the bone density of the subject W. Then, the console 18 multiplies the derived difference between the pixel values of the bone region and the soft region per unit number of pixels by a predetermined unit conversion coefficient to derive the bone density of the subject W. In this embodiment, the pixel position of the derivation region R1 used to derive the DXA profile in the DXA image data, the pixel position of the soft region of the DXA profile, and the pixel position of the bone region are predetermined according to, for example, the subject W and an imaging part.

In the radiography apparatus 16, it has been known that the charge which remains in the pixel 32 of the radiation detector 20 without being read out from the pixel 32 has an effect on radiographic image data generated by the radiation detector 20 in the next imaging operation. The charge remaining in the pixel 32 includes a component whose amount of charge varies depending on a temperature change and a component whose amount of charge varies depending on a time change.

An example of the component whose amount of charge varies depending on the temperature change is a component caused by a dark current (hereinafter, referred to as a "dark current component"). In addition, an example of the component whose amount of charge varies depending on the time change is a component which is called a lag (hereinafter, referred to as a "lag component"). The dark current component according to this embodiment is an example of a second component according to the present disclosure. The lag component according to this embodiment is an example of a first component according to the present disclosure.

The lag component is considered to be caused by a state in which some of electrons or holes generated in the pixel 32 irradiated with the radiation R transfer to a kind of metastable state and lose mobility in the pixel 32. The lag component gradually transfers from the metastable state to a conduction band over time and the mobility of the lag component is restored. However, the transition speed of the lag component is less than a change in the dark current component. Therefore, the lag component is more likely to remain in the pixel 32 than the dark current component.

Figure 10:
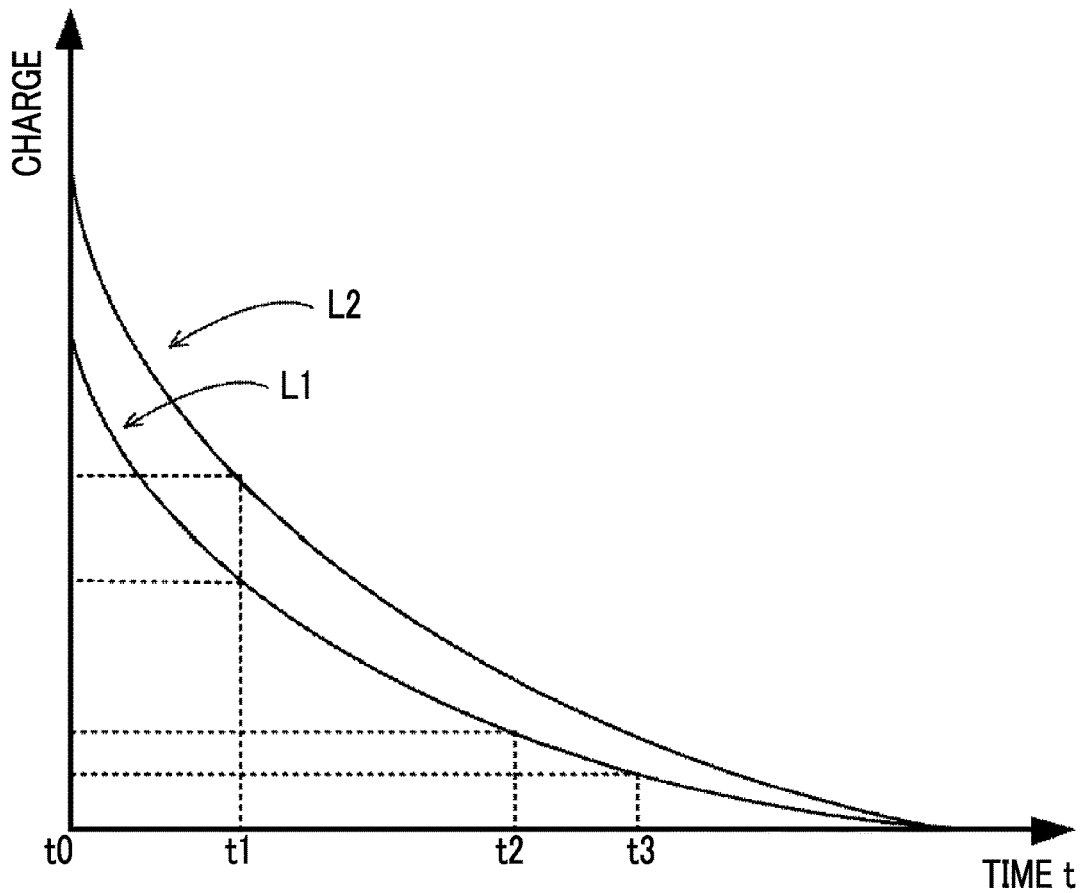
FIG. 10 is a graph illustrating a lag component.

As illustrated in FIG. 10, for the lag component, when the lag component is generated (see t0 in FIG. 10), that is, immediately after the radiography apparatus 16 is irradiated with the radiation R), the amount of charge generated in the pixel 32 per unit time is the largest and the amount of charge is gradually reduced over time. In a case in which the amount of charge when the lag component is generated is A, the time elapsed since the generation of the lag component is t, and a coefficient is α, the lag component is represented by the following Expression (1).

$$\text{Lag component} = Ae^{-\alpha t} \qquad \text{Expression (1)}$$

As illustrated in Expression (1) and the example illustrated in FIG. 10, the size (the amount of charge) of the lag component varies depending on, for example, the amount of radiation emitted to the radiography apparatus 16. FIG. 10 illustrates a state in which the amount of radiation emitted for the lag component L2 is more than that for the lag component L1. The lag components have different sizes when the lag components are generated, but have the same half-life. For example, in the example illustrated in FIG. 10, the lag component L1 and the lag component L2 have a half-life of t1.

In order to remove the dark current component and the lag component from the image data of the radiographic image, the radiography apparatus 16 turns off the thin film transistor 32B of the pixel 32 at a predetermined time in a state in which the radiation R is not emitted, reads out charge from the pixel 32, acquires offset image data, and corrects the radiographic image data using the acquired offset image data. The offset image data according to this embodiment is an example of correction image data according to the present disclosure.

However, the size (amount) of the lag component included in the offset image data varies depending on the time when the offset image data is acquired. For example, for offset image data 1 acquired at an elapsed time t1 and offset image data 2 acquired at an elapsed time t2 in the example illustrated in FIG. 10, in a case in which there is no temperature change between the elapsed time t1 and the elapsed time t2, the dark current component does not change as in the example illustrated in FIG. 11. In contrast, in the offset image data 2, the amount of lag component is reduced.

As such, the lag component varies over time. Therefore, in a case in which the radiographic image of the subject W is captured before the lag component completely flows from the pixel 32, it is difficult to appropriately correct radiographic image data even though the offset image data is used without any change. For example, a case in which the radiographic image of the subject W is captured at an elapsed time t3 in the example illustrated in FIG. 10 will be described. In this case, assuming that a change in an error range or a change in an allowable range is negligible and there is no temperature change between the elapsed time t1 and the elapsed time t2, in a case in which the radiographic image data is corrected using the offset image data 2, it is possible to correct the dark current component. Here, the term "complete" may be considered to be "complete" in a case in which, for example, an error is negligible. In addition, the lag component that does not vary over time can be removed by, for example, correction. Therefore, the lag component that does not vary over time may remain.

However, as illustrated in FIG. 10, for the amounts of lag components at the elapsed time t2 and the elapsed time t3, the amount of lag component at the elapsed time t3 is small. Therefore, even in a case in which the radiographic image data is corrected using the offset image data 2, it is difficult to appropriately correct the lag component. Here, the amount of lag component changed between the elapsed time t2 and the elapsed time t3 is very small. Therefore, in a case in which the radiation detector 20 is irradiated with a large amount of radiation and a large amount of charge is generated in the pixel 32 according to the amount of radiation, the influence of a variation in the lag component may not be brought into question (may not be considered). However, in a case in which the radiation detector 20 is irradiated with a small amount of radiation and a small amount of charge is generated in the pixel 32 according to the amount of radiation, the influence of the variation in the lag component may be significant.

Figure 12:
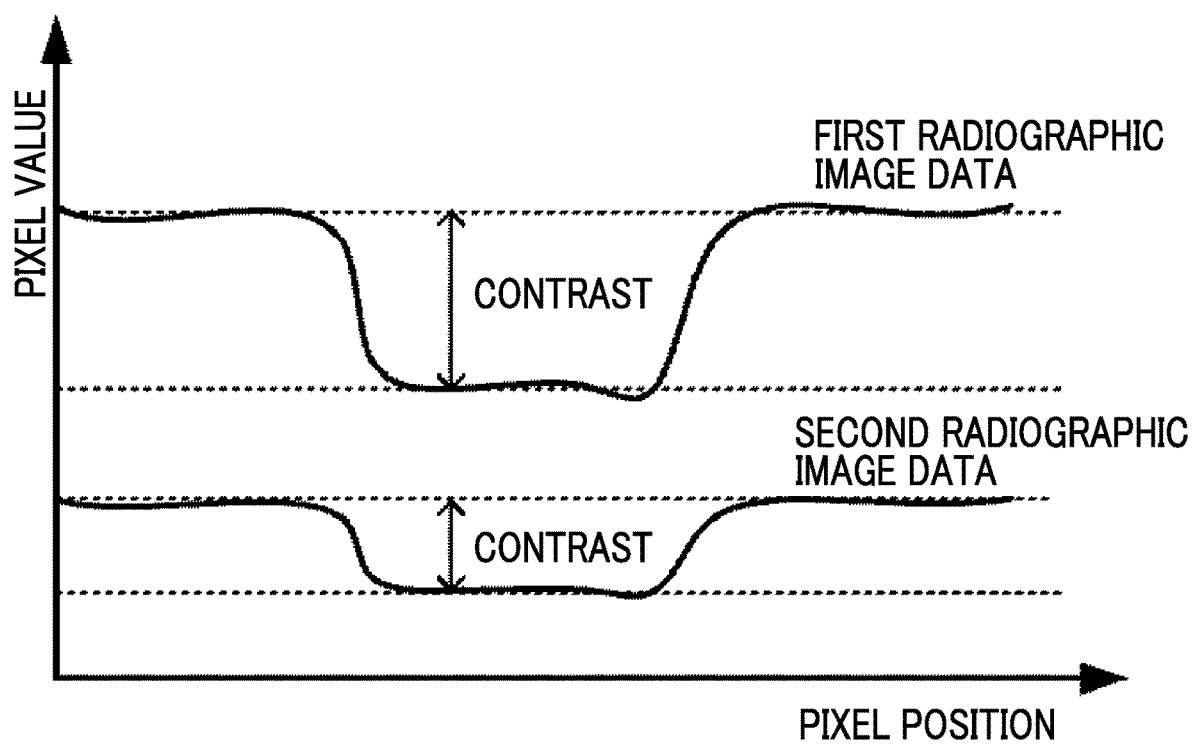
FIG. 12 is a graph illustrating the influence of the lag component on image data used to derive bone density.

As described above, in the radiography apparatus 16 according to this embodiment, since the radiation R is absorbed by the first radiation detector 20A and the radiation limitation member 24, the amount of radiation that reaches the second radiation detector 20B is less than the amount of radiation that reaches the first radiation detector 20A. In particular, in the derivation of bone density, for example, as illustrated in FIG. 12, the contrast (the ratio of the pixels in the soft region to the pixels in the bone region) of the second radiographic image data is lower than that of the first radiographic image data. FIG. 12 illustrates a profile of the first radiographic image data in a region corresponding to the derivation region R1 and a profile of the second radiographic image data in a region corresponding to the derivation region R1, similarly to the DXA profile.

Since the lag component has an effect on the contrast, the influence of a variation in the lag component is negligible in the first radiographic image data generated by the first radiation detector 20A. However, the influence of the variation in the lag component is not negligible in the second radiographic image data generated by the second radiation detector 20B.

For this reason, in this embodiment, the console 18 corrects the second radiographic image data generated by the second radiation detector 20B on the basis of the offset image data, in which the lag component and the dark current component are appropriate, to improve the accuracy of correction of the second radiographic image data, thereby improving the accuracy of deriving bone density.

Next, the operation of the radiography apparatus 16 according to this embodiment will be described.

Figure 13:
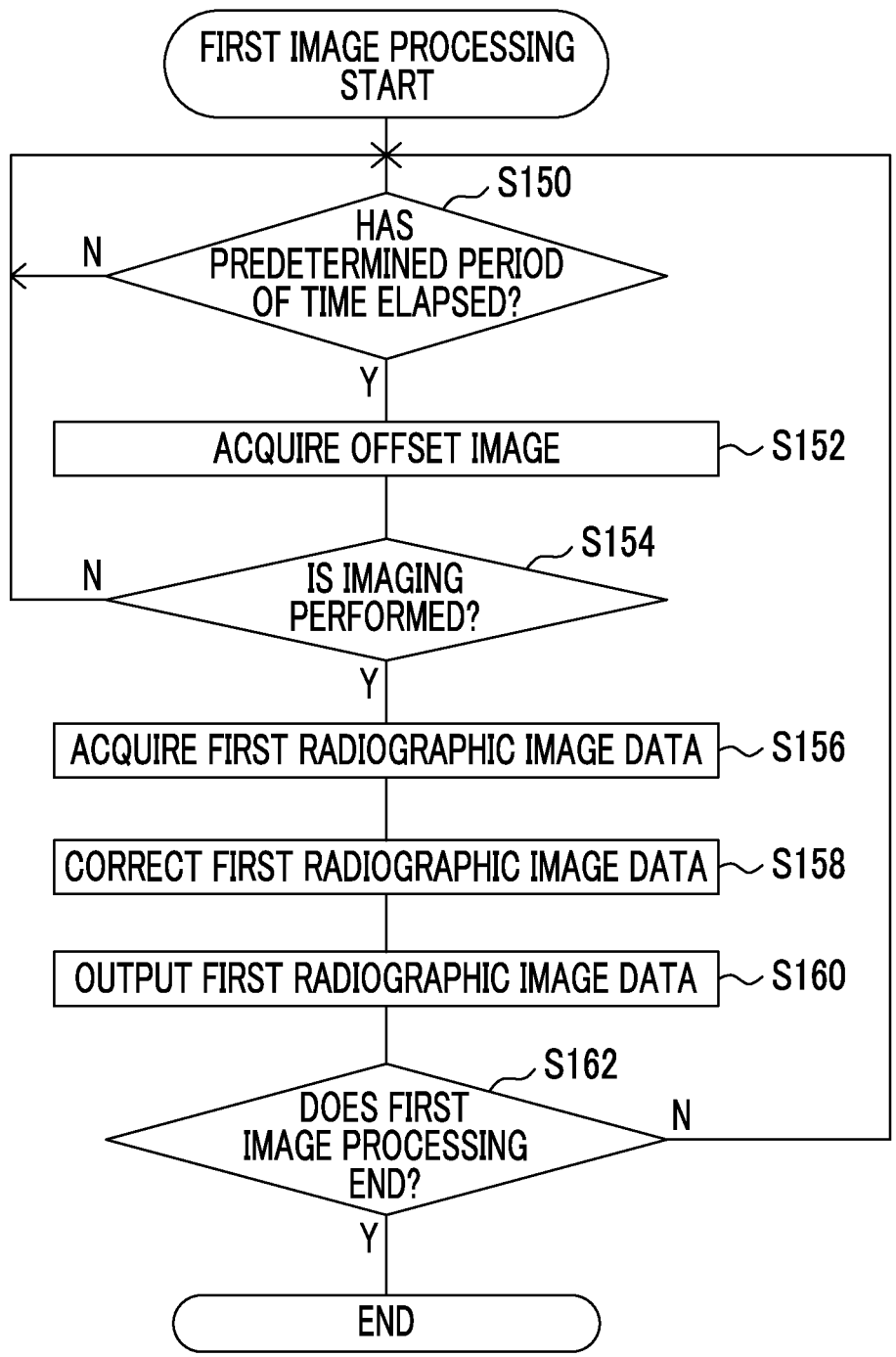
FIG. 13 is a flowchart illustrating an example of the flow of first image processing performed by a control unit of the first radiation detector in the radiography apparatus according to the embodiment.

First, image processing for the first radiographic image data generated by the first radiation detector 20A will be described. FIG. 13 is a flowchart illustrating an example of the flow of first image processing performed by the control unit 58A of the first radiation detector 20A in the radiography apparatus 16 according to this embodiment. In this embodiment, in a case in which the first radiation detector 20A receives a command to capture a radiographic image (or to start preparation for imaging) from the console 18, the control unit 58A executes a first image processing program stored in the memory 62 to perform the first image processing illustrated in FIG. 13. In a case in which the CPU 60 of the control unit 58A according to this embodiment executes an image processing program, the control unit 58A according to this embodiment functions as an example of a third correction unit according to the present disclosure.

Figure 11:
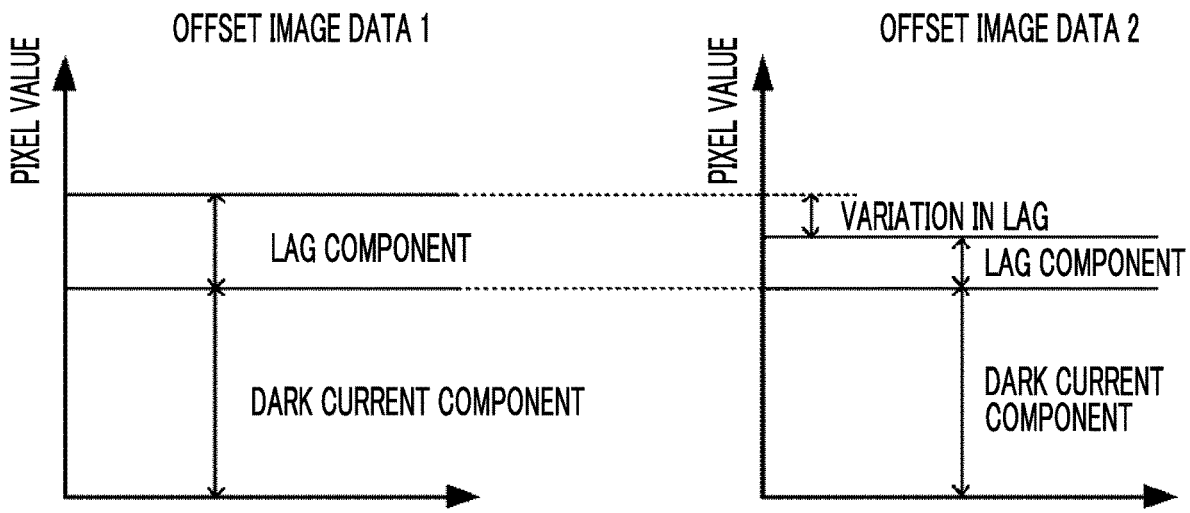
FIG. 11 is a diagram a change in a dark current component and the lag component in offset image data.

In Step S150 of FIG. 13, the control unit 58A determines whether a predetermined period of time has elapsed. The radiation detector 20 according to this embodiment acquires offset image data whenever the predetermined period of time elapses. It is preferable that the predetermined period of time is the time for which the dark current component does not change as illustrated in FIG. 11. In addition, the time for which a change in the dark current component caused by a temperature change is considered not to occur or the amount of change is in an allowable range may be obtained in advance by experiments.

The control unit 58A determines whether the predetermined period of time has elapsed using, for example, a timer (not illustrated). In a case in which the predetermined period of time has not elapsed, the determination result in Step S150 is "No" and the control unit 58A changes to a standby state. On the other hand, in a case in which the predetermined period of time has elapsed, the determination result in Step S150 is "Yes" and the process proceeds to Step S152.

In Step S152, the control unit 58A acquires offset image data from the first radiation detector 20A.

Then, in Step S154, the control unit 58A determines whether to perform an imaging operation. In a case in which an image operation is performed, specifically, in a case in which the user inputs a command to direct the radiation source 14 to emit the radiation R, the radiography apparatus 16 according to this embodiment determines to perform an imaging operation. In addition, the user inputs the command to emit the radiation R with, for example, an irradiation switch (not illustrated) and the command is input to the radiography apparatus 16 through the console 18.

In a case in which the imaging operation has not been performed, the determination result in Step S154 is "No" and the process returns to Step S150. The above-mentioned process is repeated to acquire offset image data at a predetermined time interval. On the other hand, in a case in which the imaging operation is performed, the determination result in Step S154 is "Yes" and the process proceeds to Step S156.

In Step S156, the control unit 58A acquires the first radiographic image data generated by the first radiation detector 20A (TFT substrate 30A). Then, in Step S158, the control unit 58A corrects the first radiographic image data using the offset image data. Here, the offset image data used to correct the first radiographic image data is offset image data acquired at the time that is closest to the time when imaging is performed. Then, in Step S160, the control unit 58A outputs the corrected first radiographic image data to the radiography apparatus 16.

Then, in Step S162, the control unit 58A determines whether to end the first image processing. In a case in which a radiographic image is continuously captured, the determination result in Step S162 is "No" and the process returns to Step S150. Then, the first image processing is repeated. On the other hand, in a case in which the capture of the radiographic image ends, the determination result in Step S162 is "Yes" and the control unit 58A ends the first image processing.

Figure 14:
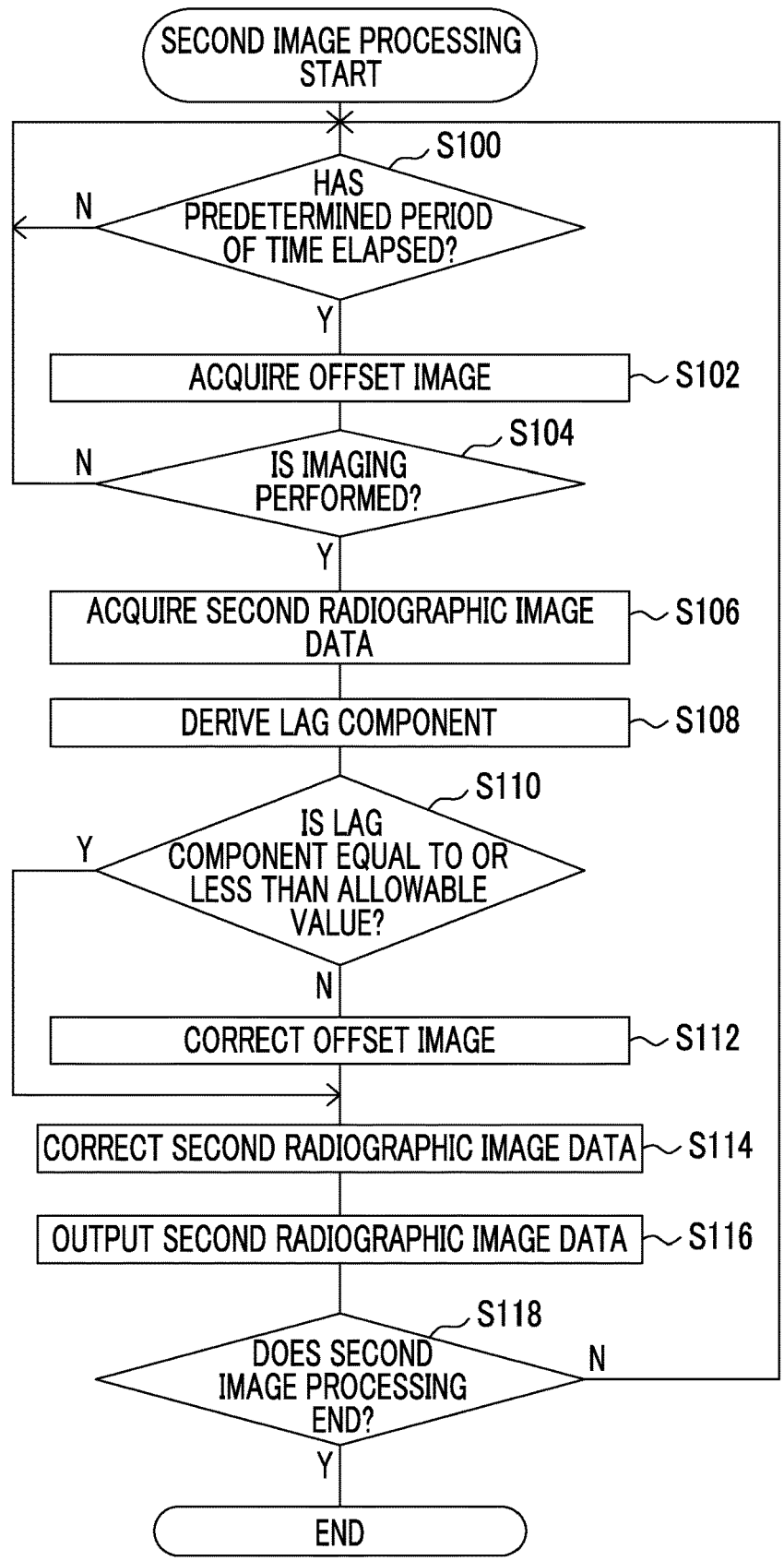
FIG. 14 is a flowchart illustrating an example of the flow of second image processing performed by a control unit of the second radiation detector in the radiography apparatus according to the embodiment

Next, image processing for the second radiographic image data generated by the second radiation detector 20B will be described. FIG. 14 is a flowchart illustrating an example of the flow of second image processing performed by the control unit 58B of the second radiation detector 20B in the radiography apparatus 16 according to this embodiment. In this embodiment, in a case in which the second radiation detector 20B receives a command to start to capture a radiographic image (or to start preparation for imaging) from the console 18, the control unit 58B executes a second image processing program stored in the memory 62 to perform the second image processing illustrated in FIG. 14 as in the second radiation detector 20A. In a case in which the CPU 60 of the control unit 58B according to this embodiment performs an image processing program, the control unit 58B according to this embodiment functions as an example of a first correction unit and a second correction unit according to the present disclosure.

In Step S100 of FIG. 14, the control unit 58B determines whether a predetermined period of time has elapsed. The predetermined period of time determining the time when the offset image data is acquired in the second radiation detector 20B is the same as the predetermined period of time in the first radiation detector 20A.

The control unit 58B determines whether the predetermined period of time has elapsed using, for example, a timer (not illustrated). In a case in which the predetermined period of time has not elapsed, the determination result in Step S100 is "No" and the control unit 58B changes to a standby state. On the other hand, in a case in which the predetermined period of time has elapsed, the determination result in Step S100 is "Yes" and the process proceeds to Step S102.

In Step S102, the control unit 58B acquires offset image data from the second radiation detector 20B.

Then, in Step S104, the control unit 58B determines whether to perform an imaging operation, similarly to the control unit 58A (see Step S154 of FIG. 13). In a case in which the imaging operation has not been performed, the determination result in Step S104 is "No" and the process returns to Step S100. The above-mentioned process is repeated to acquire offset image data at a predetermined time interval. On the other hand, in a case in which the imaging operation is performed, the determination result in Step S104 is "Yes" and the process proceeds to Step S106. Then, in Step S106, the control unit 58B acquires the second radiographic image data generated by the second radiation detector 20B (TFT substrate 30B).

Then, in Step S108, the control unit 58B derives (estimates) the lag component that remains in the pixel 32 at the time when the imaging operation is performed. As described above, the lag component is represented by the above-mentioned Expression (1). Therefore, in the radiography apparatus 16 according to this embodiment, the coefficient α is obtained in advance by, for example, experiments and information indicating the coefficient α is stored as the lag component time change information 65 in the storage unit 64 of the control unit 58B in advance.

Then, even in a case in which the amount of charge A when the lag component is generated in Expression (1) is unclear, it is possible to estimate the lag component, using at least two combinations of the offset image data and the time elapsed since the generation of the lag component, that is, since the capture of the previous radiographic image in the acquisition of the offset image data.

For example, in the example illustrated in FIG. 10, it is possible to estimate the lag component at the elapsed time t3 when imaging is performed, on the basis of a combination of the elapsed time t1 and the offset image data 1, a combination of the elapsed time t2 and the offset image data 2, and the lag component time change information 65.

Here, it is preferable to use offset image data items in which the lag component changes sufficiently as the offset image data used to derive the lag component at the time when imaging is performed, in order to increase the accuracy of deriving the lag component. For example, preferably, a variation in the lag component capable of obtaining a sufficiently high accuracy is obtained in advance by experiments, the obtained variation is used as a threshold value, and a combination of the offset image data items in which a change in the lag component is equal to or greater than the threshold value is used. As illustrated in FIG. 10 or Expression (1), a variation in the lag component when the lag component is generated is large and is reduced over time. Therefore, as the time elapsed since the lag component has been generated increases, the acquisition time interval between the offset image data items used to derive the lag component increases.

Then, in Step S110, it is determined whether the lag component derived in Step S108 is equal to or less than an allowable value. In a case in which the amount of lag component that remains in the pixel 32, that is, is included in the generated second radiographic image data is small and random noise is superimposed on the second radiographic image data, the correction of the lag component may cause an increase in the amount of random noise component and cause a reduction in the accuracy of correcting the second radiographic image data. For this reason, the control unit 58B according to this embodiment obtains an allowable value for the lag component in advance through, for example, experiments, considering influence on the second radiographic image data, specifically, influence on the derivation of bone density, and does not correct the derived lag component in a case in which the lag component is equal to or less than the allowable value.

Therefore, in a case in which the lag component derived in Step S108 is equal to or less than the allowable value, the determination result in Step S110 is "Yes" and the process proceeds to Step S114. In this case, in Step S114, the control unit 58B corrects the second radiographic image data, using the offset image data acquired at the time that is closed to the time when imaging is performed.

On the other hand, in a case in which the lag component derived in Step S108 is greater than the allowable value, the determination result in Step S110 is "No" and the process proceeds to Step S112. In Step S112, the control unit 58B corrects the lag component of the offset image data on the basis of the lag component derived in Step S108. Then, in Step S114, the control unit 58B corrects the second radiographic image data on the basis of the offset image data corrected in Step S114.

Then, in Step S116, the control unit 58B outputs the corrected second radiographic image data to the radiography apparatus 16.

Then, in Step S118, the control unit 58B determines whether to end the second image processing. In a case in which a radiographic image is continuously captured, the determination result in Step S118 is "No" and the process returns to Step S100. Then, the second image processing is repeated. On the other hand, in a case in which the capture of the radiographic image ends, the determination result in Step S118 is "Yes" and the control unit 58B ends the second image processing.

Then, the first radiographic image data output from the control unit 58A and the second radiographic image data output from the control unit 58B are input to the console 18 and are temporarily stored in the storage unit 88 of the console 18.

Figure 15:
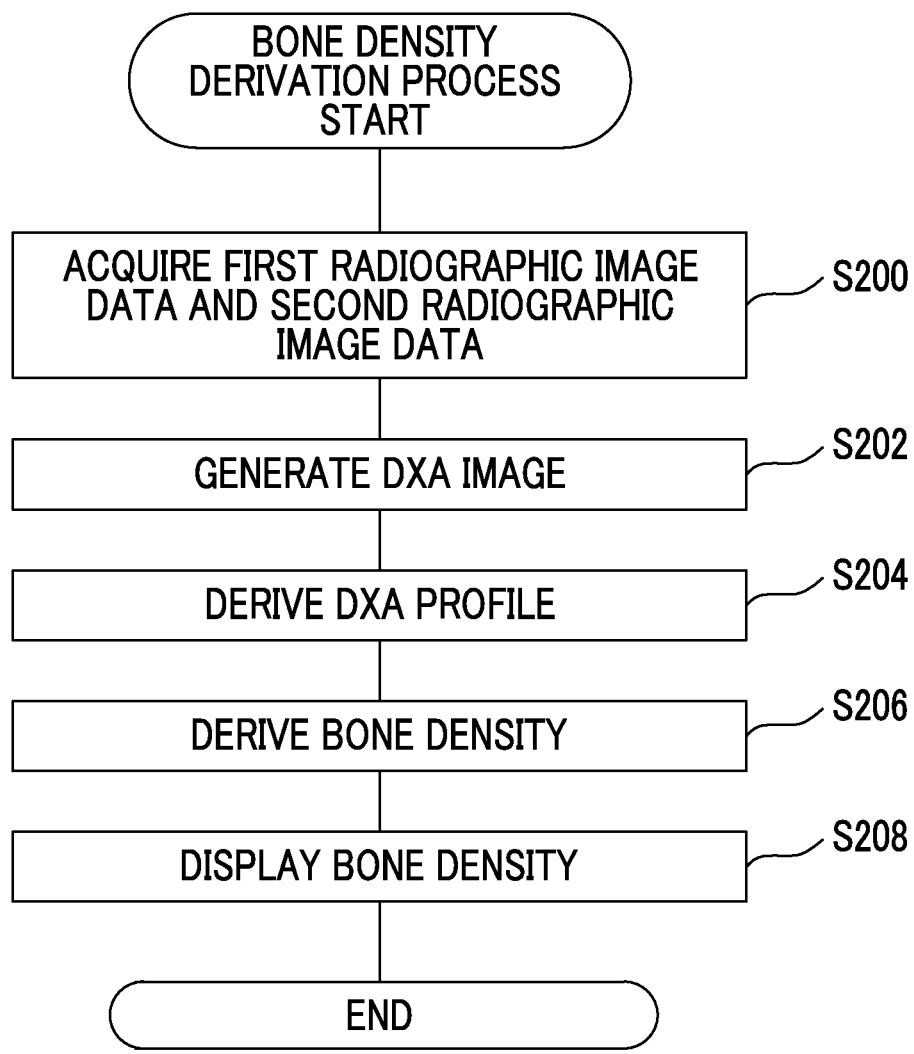
FIG. 15 is a flowchart illustrating an example of the flow of a bone density derivation process performed by a control unit of the console according to the embodiment.

In a case in which the user inputs a command to derive bone density through the operation unit 94, the CPU 82 of the control unit 80 in the console 18 according to this embodiment executes a bone density derivation processing program stored in the ROM 84 to perform a bone density derivation process illustrated in FIG. 15. FIG. 15 is a flowchart illustrating an example of the flow of the bone density derivation process performed by the control unit 80 of the console 18 according to this embodiment. In a case in which the CPU 82 of the control unit 80 according to this embodiment performs the bone density derivation processing program, the control unit 80 according to this embodiment functions as an example of a derivation unit according to the present disclosure.

In Step S200 of FIG. 15, the control unit 80 acquires the first radiographic image data and the second radiographic image data. In this embodiment, for example, the control unit 80 acquires the first radiographic image data and the second radiographic image data from the storage unit 88.

Then, in Step S202, the control unit 80 generates DXA image data (DXA image) using the first radiographic image data and the second radiographic image data as described above. Then, in Step S104, the control unit 80 derives a DXA profile using the DXA image data as described above.

Then, in Step S206, the control unit 80 derives bone density using the DXA image data as described above. Then, in Step S208, the control unit 80 displays the derived bone density on the display unit 92 and ends the bone density derivation process.

As described above, the control unit 58B of the radiography apparatus 16 according to this embodiment corrects the lag component included in the offset image data, on the basis of a combination of the offset image data, which is generated by the second radiation detector 20B in a state in which the radiation R is not emitted for the period from the end of a first imaging operation of generating the second radiographic image data using the second radiation detector 20B in a state in which the radiation R is emitted to the start of a second imaging operation of generating the second radiographic image data using the second radiation detector 20B in the state in which the radiation R is emitted and at each of a plurality of different times elapsed since the first imaging operation, and the time elapsed since the first imaging operation, the lag component time change information 65 indicating a change in the lag component, which varies depending on time in the charge remaining in a plurality of pixels 32, over time, and the time from the end of the first imaging operation to the start of a second imaging operation. In addition, the control unit 58B corrects the second radiographic image data generated from the second radiation detector 20B by the second imaging operation on the basis of the corrected offset image data.

As such, the control unit 58B according to this embodiment corrects the second radiographic image data on the basis of the offset image data including the lag component corresponding to the time when imaging is performed. Therefore, the accuracy of correcting the second radiographic image is improved.

In addition, since the control unit 80 of the console 18 derives bone density on the basis of the second radiographic image data whose correction accuracy has been improved, the accuracy of deriving bone density is improved. That is, the radiography apparatus 16 according to this embodiment improves the accuracy of correcting the second radiographic image data generated by the second radiation detector 20B irradiated with a small amount of radiation R. Therefore, it is possible to improve the accuracy of deriving bone density.

For example, the configuration and operation of the radiography system 10, the radiography apparatus 16, and the console 18 described in this embodiment are illustrative and can be changed according to situations, without departing from the scope and spirit of the invention.

For example, in this embodiment, the aspect in which the lag component is derived using a plurality of combinations of the offset image data and the time elapsed since the generation of the lag component in the acquisition of the offset image data has been described. However, the aspect in which the lag component is derived is not limited to this embodiment. For example, the lag component may be derived on the basis of the lag component time change information 65, using three or more offset image data items and the acquisition time interval between the offset image data items.

In this embodiment, the lag component of the offset image data that is used to correct the second radiographic image data generated by the second radiation detector 20B is corrected. However, the lag component of the offset image data that is used to correct the first radiographic image data generated by the first radiation detector 20A may also be corrected.

In this embodiment, the first image processing and the second image processing performed by the control unit 58A and the control unit 58B may be performed by the control unit 80 of the console 18. In addition, in a case in which the radiography apparatus 16 includes an overall control unit that controls the overall operation of the control unit 58A and the control unit 58B, the overall control unit may perform at least one of the first image processing, the second image processing, or the bone density derivation process. Furthermore, for example, another apparatus that is connected to the console 18 through the network may perform at least one of the first image processing, the second image processing, or the bone density derivation process.

The invention is not limited to this embodiment. Preferably, the radiography apparatus 16 is provided with a temperature sensor that measures the temperature of the TFT substrate 30A and the TFT substrate 30B and does not use the offset image data to correct the radiographic image data in a case in which the temperature sensor detects a temperature change equal to or more than a change in the dark current component.

In this embodiment, the case in which an indirect-conversion-type radiation detector that converts radiation into light and converts the converted light into charge is applied to both the first radiation detector 20A and the second radiation detector 20B has been described. However, the invention is not limited thereto. For example, a direct-conversion-type radiation detector that directly converts radiation into charge may be applied to at least one of the first radiation detector 20A or the second radiation detector 20B. In addition, for example, a conversion layer that absorbs radiation and converts the radiation into charge in the direct-conversion-type radiation detector is made of amorphous selenium (a-Se) and crystalline cadmium telluride (CdTe).

In this embodiment, the case in which the irradiation side sampling radiation detectors in which the radiation R is incident from the TFT substrates 30A and 30B are applied to the first radiation detector 20A and the second radiation detector 20B, respectively, has been described. However, the invention is not limited thereto. For example, a so-called penetration side sampling (PSS) radiation detector in which the radiation R is incident from the scintillator 22A or 22B may be applied to at least one of the first radiation detector 20A or the second radiation detector 20B.

In this embodiment, the case in which the console 18 derives bone density as one of the information items of the subject using the first radiographic image data and the second radiographic image data has been described. However, the derived information of the subject W is not particularly limited as long as it is obtained using the first radiographic image data and the second radiographic image data. For example, as the information of the subject W, a value indicating the information of the subject W, such as bone mineral content, may be derived using the first radiographic image data and the second radiographic image data or both bone density and bone mineral content may be derived. In addition, for example, the information of the subject W may be images such as the radiographic images of the subject W corresponding to various purposes which are obtained by so-called energy subtraction. In addition, for example, the information of the subject W may be other radiographic images of the subject used for diagnosis. In these cases, the first radiographic image data and the second radiographic image data are used as in the derivation of the bone density. Therefore, the same task as that in the case in which the bone density is derived occurs. As a result, for example, the same effect as that in this embodiment is obtained in a case in which bone mineral content is derived instead of bone density in each of the above-described embodiments.

In this embodiment, the first image processing performed by the execution of software (program) by the CPU 60 of the control unit 58A may be performed by various processors other than the CPU 60. In addition, in this embodiment, the second image processing performed by the execution of software (program) by the CPU 60 of the control unit 58B may be performed by various processors other than the CPU 60. In this embodiment, the bone density derivation process performed by the execution of software (program) by the CPU 82 of the control unit 80 may be performed by various processors other than the CPU 82.

In this case, examples of the processor include a programmable logic device (PLD) whose circuit configuration can be changed after manufacture, such as a field-programmable gate array (FPGA), and a dedicated electric circuit, such as an application specific integrated circuit (ASIC), which is a processor having a dedicated circuit configuration designed to perform a specific process. In addition, the first image processing, the second image processing, and the bone density derivation process may be performed by one of the various processors or may be performed by a combination of two or more processors of the same type or different types (for example, a combination of a plurality of FPGAs and a combination of a CPU and an FPGA). Specifically, the hardware structure of the various processors is an electric circuit obtained by combining circuit elements such as semiconductor elements.

In each of the above-described embodiments, the aspect in which the first image processing program, the second image processing program, and the bone density derivation processing program are stored (installed) in advance in the storage unit 64 of the control unit 58A, the storage unit 64 of the control unit 58B, and the ROM 84, respectively, has been described. However, the invention is not limited thereto. The image processing program may be recorded on a recording medium, such as a compact disk read only memory (CD-ROM), a digital versatile disk read only memory (DVD-ROM), or a universal serial bus (USB) memory, and then provided. In addition, each of the first image processing program, the second image processing program, and the bone density derivation processing program may be downloaded from an external apparatus through the network.

What is claimed is:

1. A radiography apparatus comprising:
a first radiation detector in which a plurality of pixels, each of which includes a conversion element that generates a larger amount of charge as it is irradiated with a larger amount of radiation, are arranged;
a second radiation detector which is provided on a side of the first radiation detector, from which the radiation is transmitted and emitted, and in which a plurality of pixels, each of which includes a conversion element that generates a larger amount of charge as it is irradiated with a larger amount of radiation, are arranged;
a first correction unit that corrects a first component, which varies depending on time in charge remaining in the plurality of pixels and is included in correction image data that is generated by the second radiation detector in a state in which the radiation is not emitted for a period from an end of a first imaging operation of generating radiographic image data using the second radiation detector in a state in which the radiation is emitted and to a start of a second imaging operation of generating radiographic image data using the second radiation detector in the state in which the radiation is emitted and at each of a plurality of different times elapsed since the first imaging operation, on the basis of a combination of the correction image data and the time elapsed since the first imaging operation, information indicating a change in the first component over time, and a time from the end of the first imaging operation to the start of the second imaging operation; and
a second correction unit that corrects the radiographic image data generated from the second radiation detector by the second imaging operation using the correction image data corrected by the first correction unit.

2. The radiography apparatus according to claim 1, wherein the correction image data includes the first component and a second component that varies depending on temperature in the charge remaining in the plurality of pixels.

3. The radiography apparatus according to claim 2, wherein the correction image data is generated at a time when a change in temperature after generation of previous correction image data is within an allowable range that is predetermined according to a variation in the second component with respect to the temperature.

4. The radiography apparatus according to claim 2, wherein, in a case in which an amount of second component in the charge remaining in the pixels of the second radiation detector in the second imaging operation is equal to or less than a predetermined threshold value, the second correction unit corrects the radiographic image data generated from the second radiation detector by the second imaging operation, using the correction image data generated at a time closest to the second imaging operation, instead of the correction image data corrected by the first correction unit.

5. The radiography apparatus according to claim 1, wherein the correction image data is generated at an interval at which a variation in the first component that is predetermined according to a change in the first component over time is equal to or greater than a threshold value.

6. The radiography apparatus according to claim 1, wherein the first correction unit corrects the first component included in the correction image data generated by the second radiation detector at a time closest to the second imaging operation.

7. The radiography apparatus according to claim 1, further comprising:
a third correction unit that corrects radiographic image data generated by the first radiation detector in the state in which the radiation is emitted, on the basis of correction image data generated by the first radiation detector in the state in which the radiation is not emitted.

8. The radiography apparatus according to claim 1, further comprising:
a derivation unit that derives information of a subject that is an imaging target, using the radiographic image data which has been generated by the second radiation detector and corrected by the second correction unit and the radiographic image data which has been generated by the first radiation detector and corrected by the third correction unit.

9. The radiography apparatus according to claim 1, wherein each of the first and second radiation detectors comprises a substrate on which the plurality of pixels are formed and a light emitting layer that is irradiated with the radiation and emits light, and
in each light emitting layer of the first and second radiation detectors, at least one of a thickness of each light emitting layer, a diameter of particles with which each light emitting layer is filled and which are irradiated with the radiation and emit light, a multi-layered structure of the particles, a filling rate of the particles, a doping amount of activator, a material forming each light emitting layer, or a layer structure of each light emitting layer is changed or a reflecting layer that reflects the light to a surface of each light emitting layer which does not face the substrate is formed on each light emitting layer.

10. An image processing apparatus that corrects radiographic image data generated by a second radiation detector of a radiography apparatus comprising a first radiation detector in which a plurality of pixels, each of which includes a conversion element that generates a larger amount of charge as it is irradiated with a larger amount of radiation, are arranged and the second radiation detector which is provided on a side of the first radiation detector, from which the radiation is transmitted and emitted, and in which a plurality of pixels, each of which includes a conversion element that generates a larger amount of charge as it is irradiated with a larger amount of radiation, are arranged, the image processing apparatus comprising:

a first correction unit that corrects a first component, which varies depending on time in charge remaining in the plurality of pixels and is included in correction image data that is generated by the second radiation detector in a state in which the radiation is not emitted for a period from an end of a first imaging operation of generating radiographic image data using the second radiation detector in a state in which the radiation is emitted and to a start of a second imaging operation of generating radiographic image data using the second radiation detector in the state in which the radiation is emitted and at each of a plurality of different times elapsed since the first imaging operation, on the basis of a combination of the correction image data and the time elapsed since the first imaging operation, information indicating a change in the first component over time, and a time from the end of the first imaging operation to the start of the second imaging operation; and a second correction unit that corrects the radiographic image data generated from the second radiation detector by the second imaging operation using the correction image data corrected by the first correction unit.

11. An image processing method that corrects radiographic image data generated by a second radiation detector of a radiography apparatus comprising a first radiation detector in which a plurality of pixels, each of which includes a conversion element that generates a larger amount of charge as it is irradiated with a larger amount of radiation, are arranged and the second radiation detector which is provided on a side of the first radiation detector, from which the radiation is transmitted and emitted, and in which a plurality of pixels, each of which includes a conversion element that generates a larger amount of charge as it is irradiated with a larger amount of radiation, are arranged, the image processing method comprising:

correcting a first component, which varies depending on time in charge remaining in the plurality of pixels and is included in correction image data that is generated by the second radiation detector in a state in which the radiation is not emitted for a period from an end of a first imaging operation of generating radiographic image data using the second radiation detector in a state in which the radiation is emitted and to a start of a second imaging operation of generating radiographic image data using the second radiation detector in the state in which the radiation is emitted and at each of a plurality of different times elapsed since the first imaging operation, on the basis of a combination of the correction image data and the time elapsed since the first imaging operation, information indicating a change in the first component over time, and a time from the end of the first imaging operation to the start of the second imaging operation; and correcting the radiographic image data generated from the second radiation detector by the second imaging operation using the corrected correction image data.

* * * * *

UNITED STATES PATENT AND TRADEMARK OFFICE
CERTIFICATE OF CORRECTION

| | |
|---|---|
| PATENT NO. | : 10,736,589 B2 |
| APPLICATION NO. | : 15/974722 |
| DATED | : August 11, 2020 |
| INVENTOR(S) | : Yasufumi Oda |

It is certified that error appears in the above-identified patent and that said Letters Patent is hereby corrected as shown below:

On the Title Page

Item (74) recites "Solaris Intellectual roperty Group, PLLC". The correct name is "Solaris Intellectual Property Group, PLLC".

Signed and Sealed this
Third Day of September, 2024

Katherine Kelly Vidal
*Director of the United States Patent and Trademark Office*